(12) United States Patent
Haithcock et al.

(10) Patent No.: US 11,642,149 B2
(45) Date of Patent: May 9, 2023

(54) RADIOLUCENT GRASPING DEVICE

(71) Applicant: Jet Med Innovations, LLC, Colleyville, TX (US)

(72) Inventors: Jeffrey Haithcock, Colleyville, TX (US); Chet R. Rees, Dallas, TX (US)

(73) Assignee: Jet Med Innovations, LLC, Colleyville, TX (US)

( * ) Notice: Subject to any disclaimer, the term of this patent is extended or adjusted under 35 U.S.C. 154(b) by 279 days.

(21) Appl. No.: 17/181,014

(22) Filed: Feb. 22, 2021

(65) Prior Publication Data

US 2021/0267619 A1  Sep. 2, 2021

Related U.S. Application Data

(63) Continuation of application No. 15/848,146, filed on Dec. 20, 2017, now Pat. No. 10,959,745.

(60) Provisional application No. 62/436,469, filed on Dec. 20, 2016.

(51) Int. Cl.
| | | |
|---|---|---|
| *A61B 17/30* | (2006.01) | |
| *A61B 17/04* | (2006.01) | |
| *A61B 17/34* | (2006.01) | |
| *A61B 17/062* | (2006.01) | |
| *A61B 17/88* | (2006.01) | |
| *A61B 17/00* | (2006.01) | |
| *A61B 90/00* | (2016.01) | |
| *A61B 17/29* | (2006.01) | |
| *A61B 17/92* | (2006.01) | |

(52) U.S. Cl.
CPC .......... *A61B 17/30* (2013.01); *A61B 17/0483* (2013.01); *A61B 17/062* (2013.01); *A61B 17/3403* (2013.01); *A61B 17/8819* (2013.01); *A61B 17/92* (2013.01); *A61B 2017/0092* (2013.01); *A61B 2017/2944* (2013.01); *A61B 2017/3411* (2013.01); *A61B 2090/376* (2016.02)

(58) Field of Classification Search
CPC ... A61B 17/0483; A61B 17/062; A61B 17/30; A61B 17/3403; A61B 17/8819; A61B 17/92; A61B 17/29; A61B 17/2833; A61B 17/28; A61B 2017/0092; A61B 2017/2944; A61B 2017/3411; A61B 2017/2945; A61B 2017/2946; A61B 2017/2938; A61B 2017/2926; A61B 2090/376; A61B 18/1447; A61B 17/8894; A61B 17/8665

See application file for complete search history.

(56) References Cited

U.S. PATENT DOCUMENTS 6,461,363 B1 * 10/2002 Gadberry ............. A61B 17/122
606/139
2020/0085492 A1 * 3/2020 Hughett, Sr. ...... A61B 18/1447

* cited by examiner

*Primary Examiner* — Jocelin C Tanner
(74) *Attorney, Agent, or Firm* — Harper & Bates LLP; Shannon W. Bates; Scott L. Harper

(57) ABSTRACT

A device to be used by an operator which may grasp objects in a sterile or non-sterile field, and may facilitate the precise placement and passage of a needle or pin into tissues while using X-ray guidance. The device provides a secure hold while keeping the hands remote from the radiation field, and by permitting non-obstructed viewing of the held instrument and tissues. A radiolucent hammer may be used to help drive a needle into firm tissues without obscuring visualization.

24 Claims, 13 Drawing Sheets

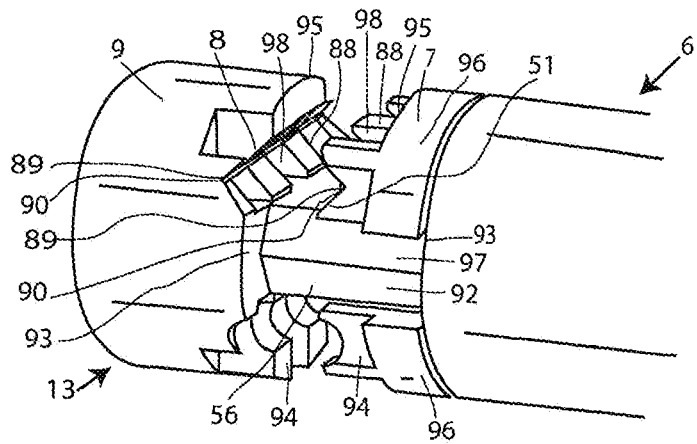
FIG 7A
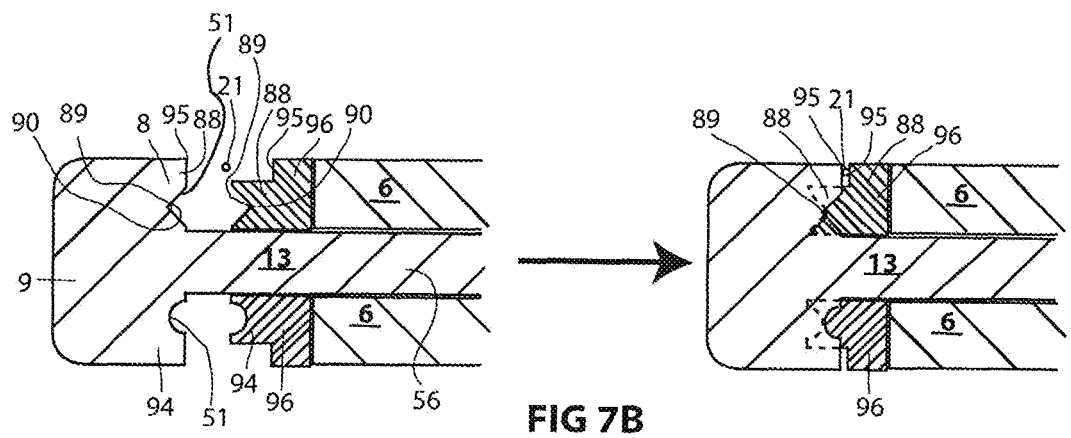
FIG 7B
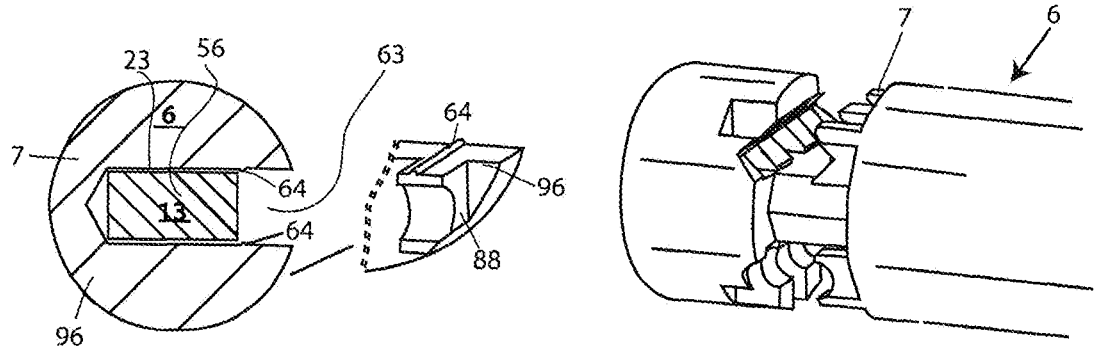
FIG 7C
FIG 7D

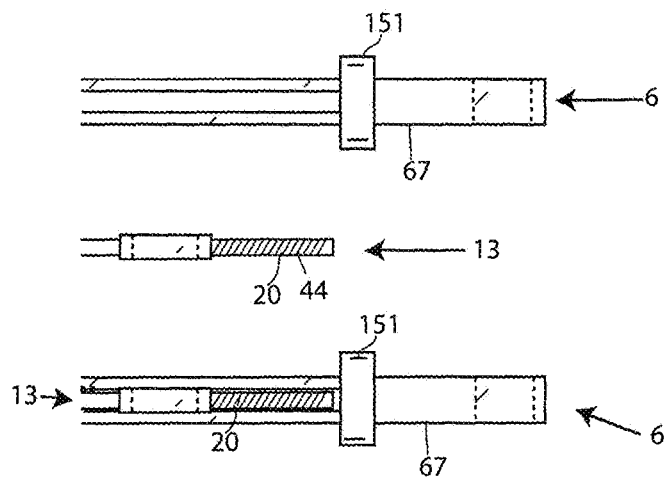
FIG 15A
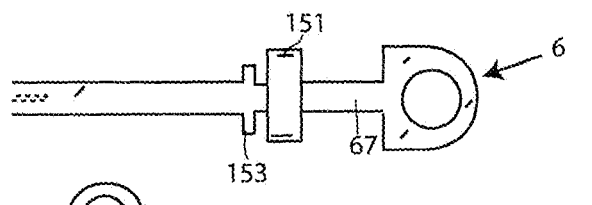
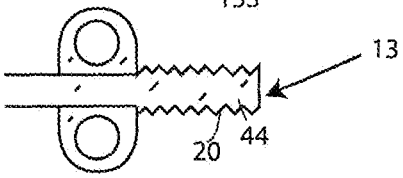
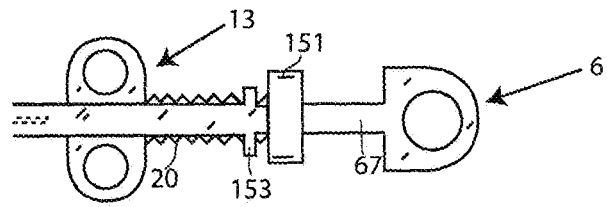
FIG 15B
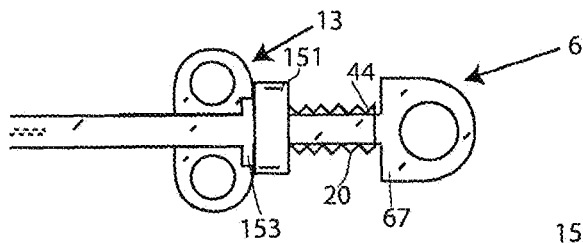
FIG 15C
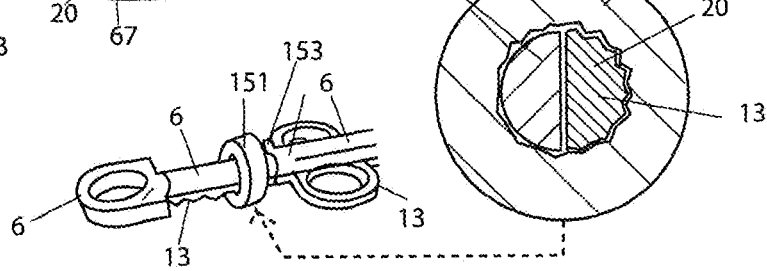
FIG 16

RADIOLUCENT GRASPING DEVICE

CROSS-REFERENCE TO RELATED APPLICATIONS

This application is a continuation of U.S. Non-Provisional patent application Ser. No. 15/848,146 filed Dec. 20, 2017 and entitled "Radiolucent Grasping Device," which claims priority to, and the benefit of U.S. Provisional Patent Application Ser. No. 62/436,469 filed Dec. 20, 2016 and entitled "Radiolucent Guidance Device for Needle or Instrument", each of which is incorporated herein by reference in its entirety for all purposes.

BACKGROUND OF THE INVENTION

Medical procedures sometimes involve the use of x-ray fluoroscopy to visualize the passage of a needle or pin or other radio-opaque (easily visible under x-ray) device through tissues which may also be moderately to highly radio-opaque. The operator's hands should not be in the direct beam so it is challenging to manipulate the medical instruments without a holding device. Current methods involve manipulation of the needle with the hands or with grasping devices which are imperfect for this purpose. Current grasping devices may not be radio-opaque, obscuring the important structures under fluoroscopy, or do not provide precise grasp of the equipment to prevent slippage, torqueing, or bending during use. Current methods also do not provide a calibrated force of grasp which can help prevent excessive passage of the needle during application of force from the hands, a hammer, or other. Also, current hammers are metallic and obscure visualization. The current invention serves to improve the described shortcomings.

BRIEF SUMMARY OF THE INVENTION

The present invention provides a device for grasping any medical devices while being controlled by the operator's hands which are grasping the invention. The invention is substantially radiolucent (permitting X-rays to pass through) and utilizes linear motion of grasping elements. In addition to such features, the invention has features specifically suited for the effective grasping of needles of various sizes, with some embodiments providing concavities in the grasping elements which cradle the needle shaft and provide a high grasping force without crushing or bending. The force is applied in a circumferential manner in some embodiments. The invention also has the ability to provide a calibrated grasping force from minimal to extremely forceful, and with a mechanical advantage that permits a greater force at the grasping end compared to the force provided by the operator. The grasp may also be locked so that it continues to grasp forcefully without any further force being applied to the invention, although other embodiments require continued input of force by operator in order to continue the force applied by invention to medical device. The former allows operator to manipulate the needle or other device without attending to the force of grasping, while the latter provides operator with constant control over grasping force.

An example of use of the invention might be the insertion of a needle into the vertebral body of the spine of a person with compression fracture, in order to inject cement (vertebroplasty or kyphoplasty procedure). The needle must be carefully passed under x-ray fluoroscopy into a specific, small target area of the bone. The invention may be used to grasp the needle and hold it while keeping the hands considerably remote from the beam, in one example approximately 18 inches from the needle. The needle is held in precise position using the desired amount of grasping force while fluoroscopy is performed. The operator may push on the invention to direct the needle into the tissues while visualizing its course under fluoroscopy. Or the operator may strike the needle or invention holding the needle, with a conventional medical hammer or novel radiolucent hammer to drive it in under visualization. The grasping force may be adjusted so that the needle can pass when hammered or pushed, but will not lurch forward excessively, possibly passing beyond the target tissue into a sensitive structure which might be damaged, such as the spinal cord or blood vessel.

Several improvements over currently available devices and methods are achieved. The shape and length of the device are optimized for the purpose described, providing precise application of force while keeping the operator at a distance. The radiolucent structure improves visualization of tissues and medical device by not interfering, whereas many current devices are made of metal for non-fluoroscopic use, and adapted for use under fluoroscopy, where their radiopaque nature can interfere with visualization of important tissues and needle. Common existing devices are often referred to as forceps, hemostats, or clamps, and are reliant on the strong resistance to lateral bending of long segments of metals. These have a scissors-like configuration, so that the grasping surfaces are at varying angles in relation to each other depending on how widely they are spread open. This may provide an uneven and non-circumferential force on the medical devices, many of which are round in cross-section. Such uneven force may crush the tubing, or allow excessive slippage in different planes. This invention provides a linear motion of the grasping elements which permits use of lightweight materials such as plastic, in configurations which minimize material volume and weight, since they can withstand the linear forces. Many current devices do not provide for customized concavities for many different needle sizes so that each is maximally grasped circumferentially. Many devices are not able to effectively grasp a choice of the small diameter needle shaft and the wider hub or handle, because the range of excursion of the grasping surfaces is not great enough to be used practically. Many devices could not grasp tightly enough or with enough precise control to provide for the optimum resistance to needle travel that may prevent excessive travel during application of in-line force by a hammer or other object. Many current devices are not rigid enough to provide for forceful guidance of a grasped needle due to bending of the device along its length due to moment arm forces. Many current devices do not provide for choices of angle of grasp of the needle, permitting the long axis of the device to be oriented optimally for application of force by operator, as well as positioning in the sometimes awkward field between image receptor and patient. The present invention includes all the above features and provides all of the above desired functions. Whereas some current devices may offer some of the above structures and qualities, we are not aware of any which provide a majority of them or the entire combination which improves the function of the invention.

The present invention includes a proximal end for handling by the operator and adjustment of grasp force in some embodiments. The middle portion is long and narrow providing length, and the distal portion provides the grasping function of the medical device. The entire structure is rigid and strong so that forces are transferred from the hands to the held instrument through the invention.

The grasp adjustment mechanisms, which are usually in the proximal end but may be elsewhere, may consist of a screw mechanism, or a lever mechanism, or a simple sliding configuration, although any mechanism that can provide linear motion of the second sliding element could be applied. The grasping mechanism includes grasping elements, which are roughly parallel to each other, and are squeezed together along a linear path so that they remain parallel. These plates may contain concave areas with radii that accommodate different needle sizes, or larger structures such as needle handle. In some embodiments, the plates are part of modular inserts which may be changed for others to accommodate the particular needle or medical device being used at the time.

BRIEF DESCRIPTION OF THE DRAWINGS

FIG. 7A-C depict an embodiment with interleaved grasping elements including a snap-on grasping element. FIG. 7D depicts a variation with grasping elements that are not removable or snap-on, having fewer parts and simplified manufacture and assembly.

FIG. 15A-C depicts a variation of FIG. 13 which includes threads and a nut to provide a locking hold.

FIG. 16 depicts a variation of the embodiment in FIG. 12 which includes threads and a nut to provide a locking hold.

DETAILED DESCRIPTION

Figure 1:
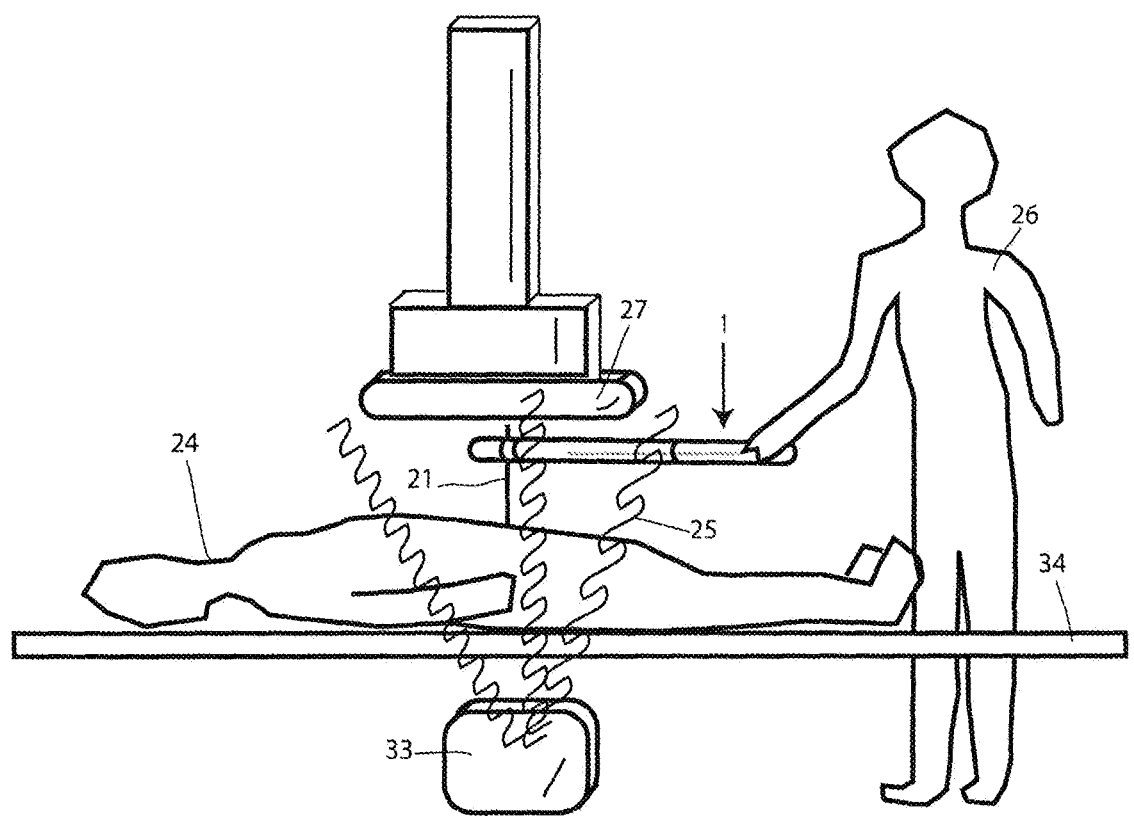
FIG. 1 is an overview of the invention being used in a medical procedure.

FIG. 1 is an overview depicting one example of use of the invention. The grasping device 1 is held in the hand of the operator 26 who uses the grasping device 1 to guide the needle 21, which is held in place by the grasping device 1, into the patient 24. X-rays 25 arise from the x-ray generator 33 and pass through the patient 24, and through the grasping device 1, to reach the image receptor 27, which forms an image that can be viewed by the operator 26 on a monitor (not depicted) in real-time as they work. The needle 21 is radio-opaque, so its position can be viewed relative to the tissues of the patient 24 which are also visible on the image. The grasping device 1 is substantially radiolucent (poorly visible under x-ray) and therefore does not interfere with visualization of important tissue structures and needle 21.

Figure 2:
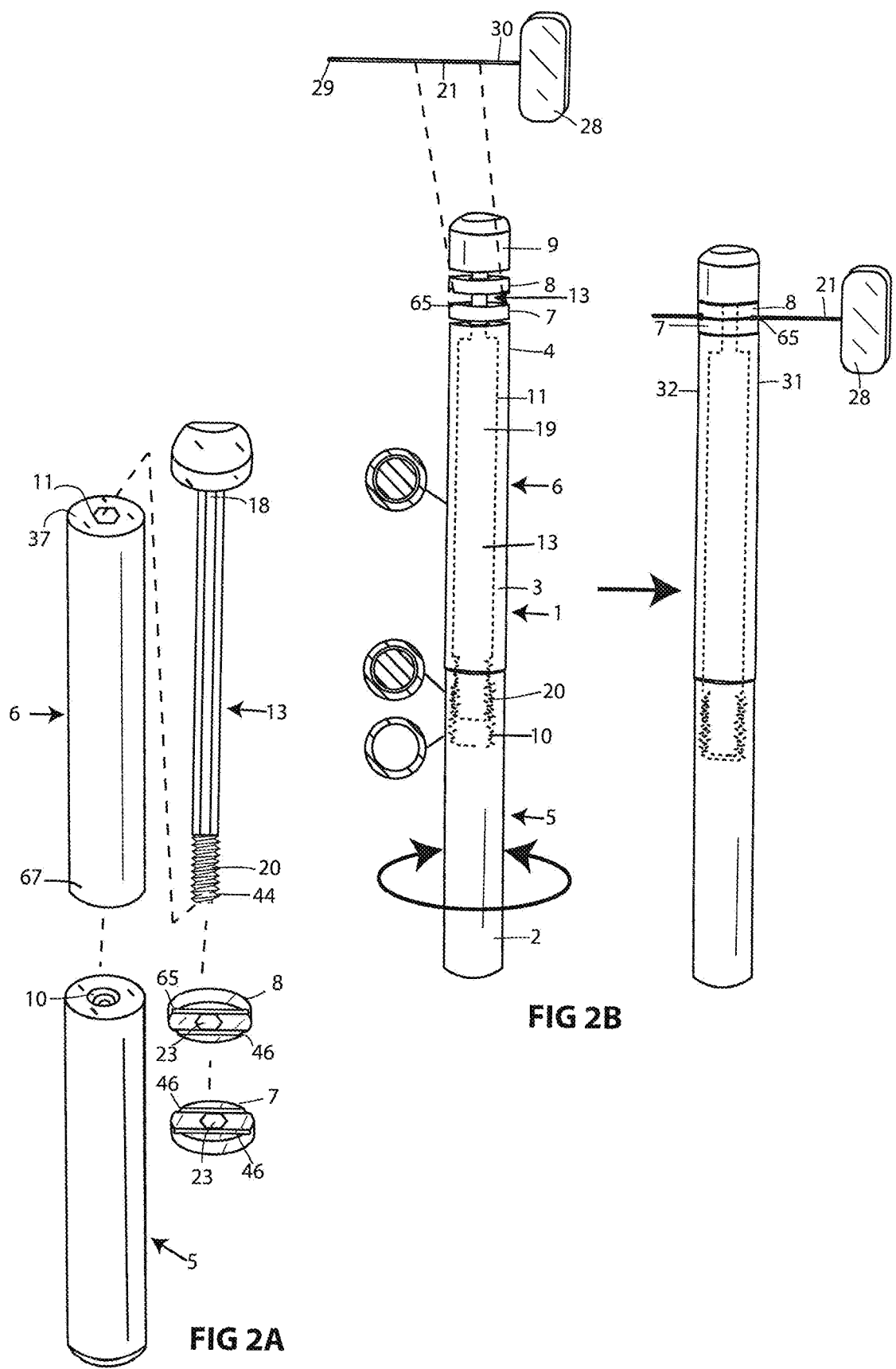
FIG. 2A-B depicts the assembly and general mechanism of action during use for an embodiment.

FIG. 2A is a perspective exploded view depicting the components and assembly of an embodiment of the grasping device 1, and FIG. 2B is a sequential perspective view with cross-sectional 2 D views corresponding to locations indicated by lines, depicting a general action of the invention including the important feature of side-entry of the needle. All elements are rigid and in this embodiment are made out of a plastic polymer.

In FIG. 2A and FIG. 2B, the device has a proximal portion 2 where the operator holds the grasping device 1, a middle portion 3, and a distal portion 4 proximate to the subject (not shown, may be a patient or other object that is having work done to it). It has a first sliding element 6 and a second sliding element 13 which are slidably attached to each other. The handle 5 is solid and rigid and contains screw threads 10 which mate with screw threads 20 on the second sliding element 13. The second sliding element 13 is solid and rigid and is hexagonal in cross section. The second sliding element head 9 contains screw threads 14 which mate with the threads 16 on the distal second sliding element 13 to provide a rigid connection between the two elements. First grasping element 7 and second grasping element 8 are slidably located on the distal second sliding element, where they may not rotate due to their hexagonal aperture 23. When assembled, the handle 5 abuts the first sliding element 6. This interface permits rotation of the handle 5 relative to the first sliding element 13. The second sliding element 13 may not rotate within the first sliding element due to hexagonal configuration of the second sliding element channel 11 and most of the second sliding element 13. Thus rotation of the handle relative to the first sliding element results in a shortening or lengthening of the joined handle 5 and second sliding element 13. Assembly of the components, depicted in FIG. 2A, is indicated by the dashed lines. The first grasping element 7 and second grasping element 8 may be slid onto the second sliding element 13 by passage of the second sliding element 13 through the second sliding element aperture 23 of the grasping elements. The first needle slot 65 and second needle slot 46 on each grasping element are depicted. Then the proximal end 44 of the second sliding element 13 is passed into the second sliding element channel 11 on the distal end 37 of the first sliding element 6, until it protrudes from the proximal end 67 of the first sliding element 6. Then screw threads 10 of the handle 5 are screwed onto the screw threads 20 of the second sliding element 13. The device is now assembled as depicted in FIG. 2B.

On the left in FIG. 2B, the grasping device 1 is configured with space between the first 7 and second 8 grasping elements. The needle 21 is passed into the device from the side as indicated by dashed lines, so that the needle 21 lines up with the appropriate needle slot 65. The handle 5 is rotated relative to the first sliding element 6, causing retraction of the second sliding element 13 deeper into the handle 5, pulling the second sliding element head 9 towards the first sliding element 6, due to the engagement of the screw threads 20 of the second sliding element and the screw threads 10 of the handle. The mid shaft 19 of the second sliding element 13 slides through the second sliding element channel 11 of the first sliding element 6. Since all components are rigid, and because the first and second grasping elements 7 and 8 are slidably positioned around the second sliding element 13, the grasping elements are pulled together tightly, engaging and rigidly securing the needle as shown to the right of the arrow. If desired, tension may be adjusted greatly enough so that severe force would be required to push the needle 21 relative to the grasping device 1. Alternatively, lesser tension would result in a less tight holding of the needle 21 so that the needle 21 would be held within the confines of the device 1 yet slidable along its longitudinal axis (up and down in this figure). This would allow removal of the needle 21 from the device 1 by an upward motion of the needle 21 such that its tip may slide through the device 1 and exit from its top 31 (herein referred to as a top exit). Due to the needle 21 having an affixed handle 28, the needle 21 might be awkward to get a bottom exit of the needle by sliding the grasping device 1 upwards, off of the needle 21 which would exit from its bottom 32. However, this may be easier with some needles with smaller or absent handles or hubs. An important feature provided by this device therefore relates to the possibility of side-entry and exit. At any time they operator may further loosen their hold of the needle by further counter-rotation of the handle, allowing the needle to exit from the side of the needle (herein referred to as side-exit). The type of needle entry and exit may be important in practice. For example, a common use is to push the needle into the subject using the invention, after which time it is desired to remove the grasping device 1 while leaving the needle 21 in place in the tissues of the body. Top exit is not possible due to the needle tip 29 being embedded in tissue, so side-entry is very convenient and useful and simple with this invention.

Figure 3:
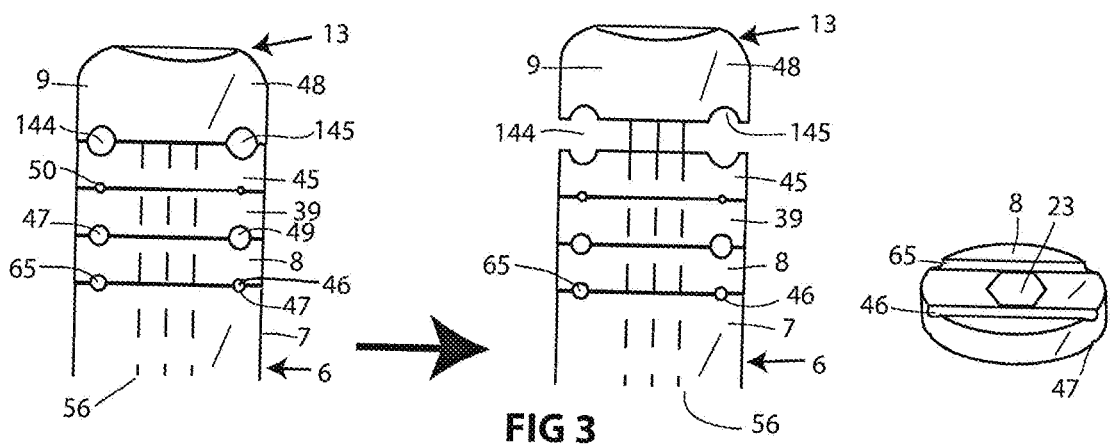
FIG. 3 depicts an embodiment utilizing multiple grasping elements to provide optimal holding of different types of objects.

FIG. 3 includes a sequence of two top views of the distal end of another embodiment, and a perspective view of one grasping element 8. This embodiment uses a plurality of grasping elements to accommodate many needle diameters. The second sliding element head 9 is rigidly attached to the second sliding element 13 which passes through the second sliding element apertures 23 of the second 8, third 39, and fourth 45 grasping elements, which are slidably configured on the second sliding element 13. The first grasping element 7 is integral with the first sliding element 6, and the fifth grasping element 48 is integral with the second sliding element 13. The hexagonal configuration of the distal shaft 56 second sliding element 13 and aperture 23 prevent their rotation relative to each other, keeping the needle slots aligned. Eight needle slots including first 65, second 46, third 47, fourth 49, fifth 50, sixth 143, seventh 144, and eighth 145 needle slots are depicted in this example. Each needle slot is partially present on adjacent grasping elements, which together form the circumferential needle slot. On the left, the second sliding element head 9 is retracted as far as possible, creating a configuration suitable to hold a needle in any slot. The second sliding element head 9 serves as a fifth grasping element 48 with two needle slots including the seventh needle slot 144 and eighth needle slot 145. Second grasping element 8 has needle slots on both sides, totaling four, including first needle slot 65, second needle slot 46, and third needle slot 47, and fourth needle slot 49. The first sliding element 6 also serves as the first grasping element 7 and has two needle slots including first needle slot 65 and second needle slot 46. On the right top view of the sequence, the second sliding element 13 and its distal shaft 56 have been moved forward by the operator, leaving a space between the second sliding element head 9 and the fourth grasping element 45, opening seventh needle slot 144 and eighth needle slot 145 to receive needles. Alternatively the operator may have manually moved the second 8 and third 39 grasping elements forward to open first needle slot 65 and second needle slot 46, or other variation to expose any pair of needle slots desired. The second sliding element 13 may then be retracted, closing the slot and tightening the hold on the needle (not depicted).

Figure 4A:
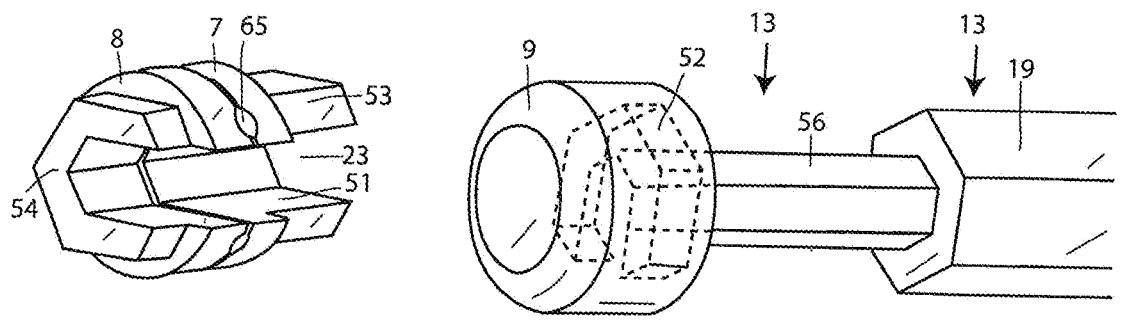
FIG. 4A-C depict an embodiment with removable grasping elements that allow the operator to change them out to accommodate different objects to be held by the device, and to enable a large second sliding element shaft in the proximal and mid portions with a smaller caliber distally which accommodates a more central location of needle slot.
Figure 4B:
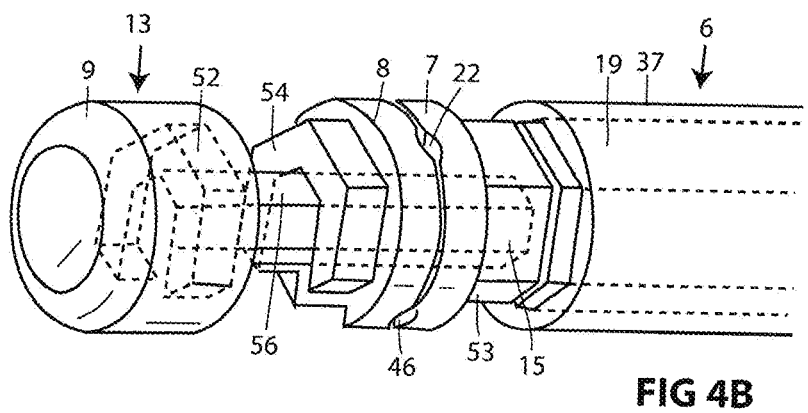
Figure 4C:
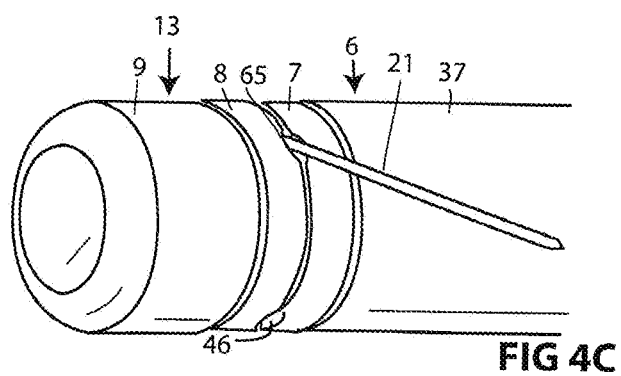

FIG. 4A-C are perspective views of a portion of an embodiment of the invention using modular, removable and replaceable grasping elements. In FIG. 4A, first 7 and second 8 grasping elements are shown positioned relative to each other as when grasping a needle (not shown) in the first 22 or second 46 needle slots, which would usually differ in size to accommodate different needle sizes. This view shows their inner surfaces 51 to be roughly "C" shaped in cross section, serving as a second sliding element aperture 23 with an open, incomplete hexagonal shape. It may be seen that these grasping elements can be rotated and placed onto distal second sliding element shaft 15 which is narrower than the mid shaft 19 of the second sliding element shaft 13 to which the distal shaft 56 of the second sliding element shaft 13 is rigidly attached. The first 7 and second 8 grasping elements are slidable on the distal shaft 56, and can be adjusted in position along the shaft relative to each other, to the second sliding element head 9, and to the distal end 37 of the rigid first sliding element 6. The second sliding element head 9 is attached rigidly to the distal shaft 15 of the second sliding element 13, and contains an engagement cut-out 52 corresponding in configuration (in negative form) to the second engagement element 54 on the second grasping element 8 to which the second engagement sub-element element 54 is rigidly attached. This second engagement sub-element 54 fits into the engagement cut-out 52 where cut-out 52 provides a detachable union providing stabilization of the removable and replaceable second grasping element 8. Similarly, the first grasping element 7 includes a first engagement sub-element 53 having a larger width than the distal shaft 56, and which may be slid proximally until abutting the larger mid second sliding element shaft 19. In FIG. 4B, the pieces have been assembled as described and the second sliding element 13 has been passed inside the first sliding element 6. The needle (not shown) may be placed into the needle slot 65 and the second sliding element 13 retracted in the direction of the arrow, thereby retracting the second sliding element head 9, and compressing the two grasping elements between the second sliding element head 9 and the distal first sliding element 37, grasping the needle as tightly as desired. FIG. 4C depicts the system grasping the needle 21 in fully retracted position.

Figure 5:
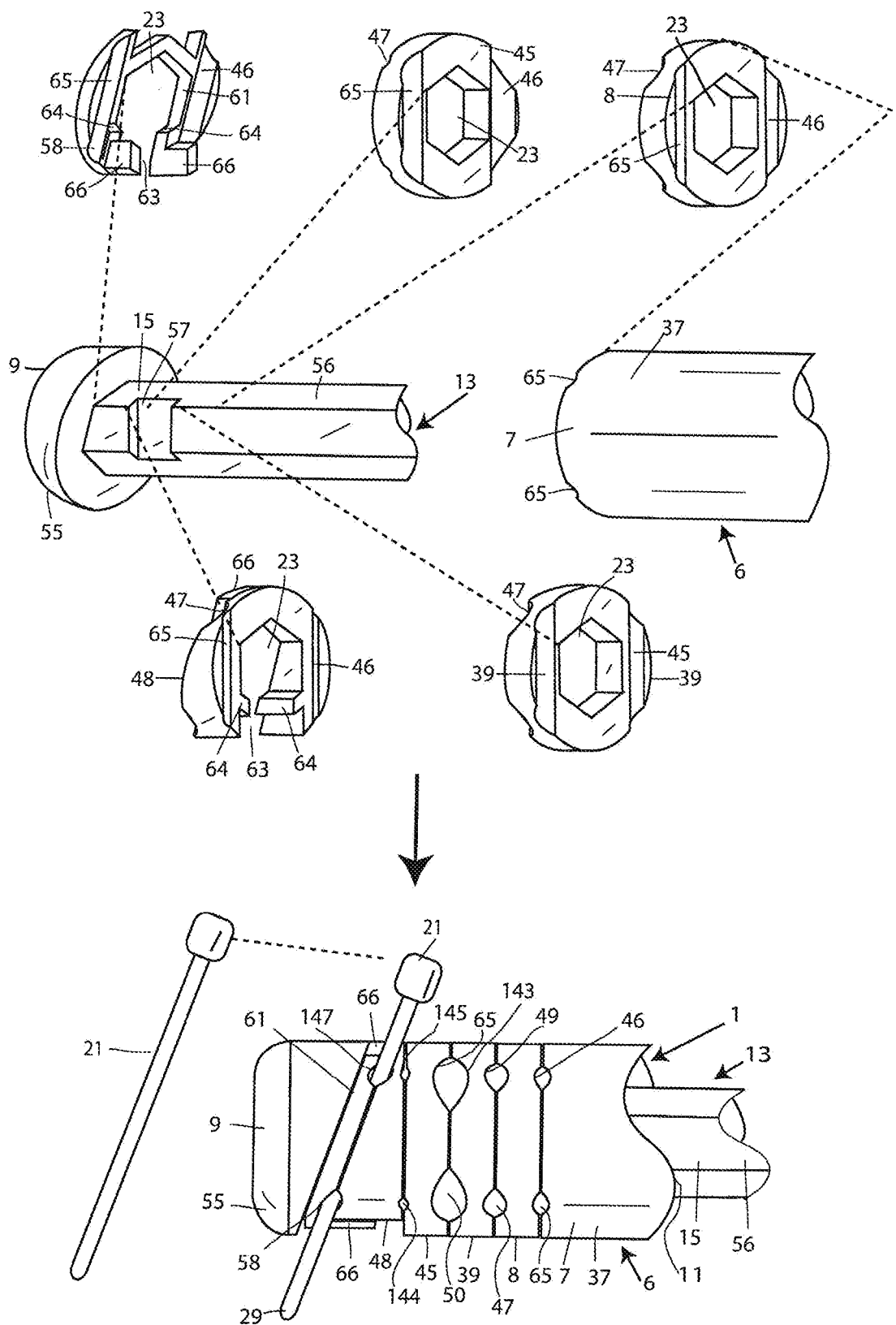
FIG. 5 depicts an embodiment with a plurality of snap-on grasping elements and straight and angled needle slots.

FIG. 5 includes an exploded perspective view of the distal end of an embodiment of the invention, and a side view of the assembled device below the arrow indicating assembly. This embodiment includes features of grasping elements providing a slanted needle angle, a wedge-shaped second sliding element head to improve slanted needle function, means to stabilize components, and insertable and replaceable snap-on grasping elements. All components are rigid and may be composed of a substance such as hard plastic. The distal portion 15 of the second sliding element 13 includes a second sliding element head 9 with a modified shape roughly like a wedge in side view. This permits the needle tip 29 to exit the grasping device 1 very close to tip 55 of grasping device 1, decreasing the distance between subject (not shown) and bottom portion of needle slot 58 when the device is angled, since the tip acts a pivot point. The distal second sliding element shaft 56 contains a notch 57. There is a total of six grasping elements and ten needle slot pairs to accommodate eight different needle diameters in a straight orientation, and two in a slanted orientation. The first grasping element 7 is provided by the distal portion 37 of the first sliding element 6 which has first 65 and 46 second needle slots. The third needle slot is located on opposite side of the second grasping element 8 from first needle slot 65, and the fourth needle slot 49 is likewise opposite of the second needle slot 46 on the second grasping element 8. The fifth 50, sixth 143, seventh 144, eighth 145, ninth 146, and tenth 147 needle slots are similarly disposed on the third 39, fourth 45, fifth 48, and sixth 61 grasping elements as depicted. The second 8, third 39, and fourth 45 grasping elements provide for grasping a needle or other object in a straight orientation (orthogonal to long axis of grasping device 1), and contain the needle slots, and a hexagonal second sliding element aperture 23 through which the second sliding element 13 may pass during assembly, providing for a slidable, non-rotatable attachment between second sliding element 13 and said grasping elements. Fourth grasping element 45 may be positioned over the second sliding element shaft notch 57 once assembled, but maintains same slidable, non-rotatable relationship as when positioned over portions of second sliding element 13. All grasping elements cannot move substantially in an orthogonal direction relative to the second sliding element 13. Fifth 48 and sixth 61 grasping elements provide for a slanted orientation of needle, non-orthogonal to long axis of grasping device 1, and are removable and replaceable with others that are similar (not shown) except for needle slot size, in order to accommodate a plurality of needle sizes in the slanted orientation. Such replacement may occur without passing of fifth 48 and sixth 61 grasping elements over the end of the second sliding element, because their second sliding element apertures 23 each have an opening 63 allowing the element to slide on or off of the second sliding element 13 at the notch 57, from where they may slide distally to the distal end of the second sliding element 15 for use, where they are attached in a slidable and non-rotatable relationship, and are not able to move orthogonally to second sliding element 13. The distance between the two tabs 64 of each fifth 48 and sixth 61 grasping element is very slightly greater than the width of the distal second sliding element 13 where the notches 57 are present on both sides (only depicted on one side but symmetrically disposed on the opposite side) providing for their removable function. During use, the second sliding element 13 is retracted using means similar to described herein, for example FIG. 3. This compresses all the grasping elements between the second sliding element head 9 and first sliding element 6. Because the fifth 48 and sixth 61 elements have an interface between them which is roughly slanted, or non-orthogonal to the long axis of the grasping device 1, there could potentially be forces pushing them perpendicular to the long axis of the second sliding element 13. The shape of their apertures 23 and tabs 64 prevent sliding in these direction, and overhangs 66 are present in this example to block such motion. In variation, these overhangs 66 may be absent. When assembled as in the side view, all grasping elements nest together as shown, providing for the ability to hold appropriately sized needles in each needle slot pair.

To use this invention, assembly of the parts may occur at manufacture or by operator. The second 8, third 39 and fourth 45 grasping elements may be placed over the proximal second sliding element shaft (not depicted) and slid down to the distal second sliding element shaft 56. Not depicted in this figure but referring to the elements in FIG. 3, the second sliding element may then be inserted into the distal first sliding element 37 until protruding from the proximal first sliding element, and then the handle may be screwed onto the second sliding element threads. Fifth 48 and sixth 61 grasping elements may be assembled as described above, and then the device is ready for use. Needle 21 may be placed in the needle slots from a side approach if desired.

In variation, more grasping elements may be added in this stacked configuration to accommodate more needle diameters, or with slots of different configurations more suitable for non-needle instruments, or non-shaft portion of needles. For example, the grasping surfaces may be smooth without slots, for grasping substantially flat objects. Or a semispherical concavity could be in the place of the depicted needle slots, for grasping of a predominantly spherical object. Many different configurations are possible and within the scope of this invention. Variations could include non-wedge shaped second sliding element head with corresponding changes in configuration of sixth grasping element to provide for straight or slanted needle slot of adjacent grasping elements, as desired. Any number of grasping elements may have open or closed apertures to permit side mounting or end mounting onto the second sliding element shaft.

Figure 6A:
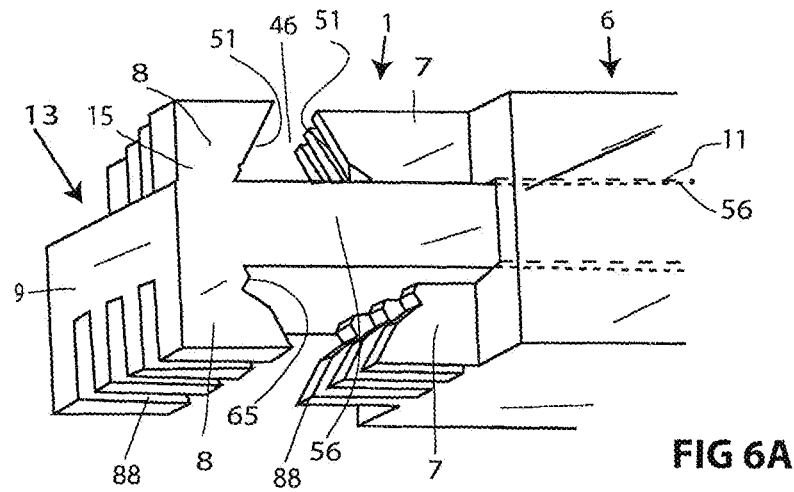
FIG. 6A-C depicts an embodiment with interleaved grasping elements, providing for a simplified manufacture and assembly with fewer parts.
Figure 6B:
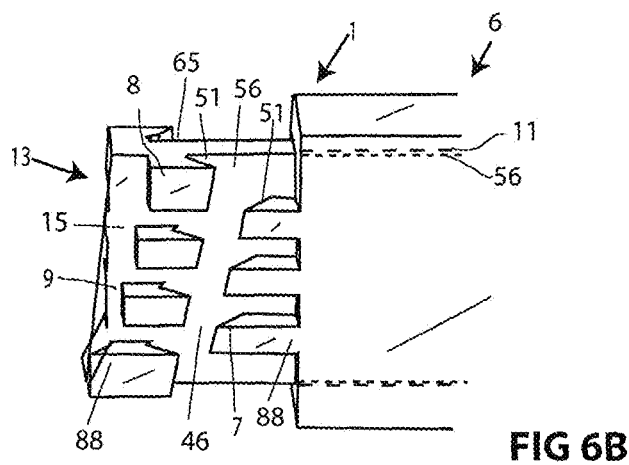
Figure 6C:
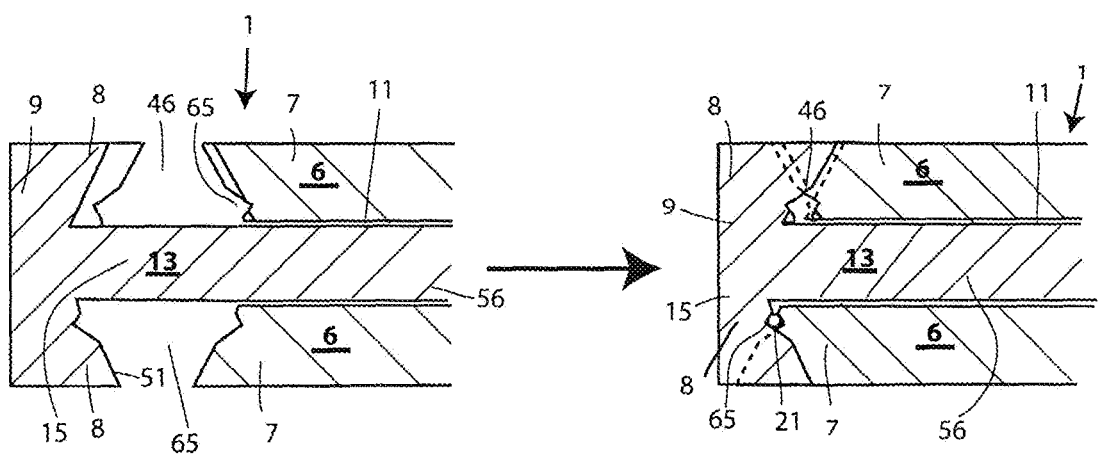

FIG. 6A-C depict two perspective views (FIG. 6A) and a sequential longitudinal thick cross-section side view through the longitudinal centerline (FIG. 6C) of the distal portion of another embodiment which includes interleaved grasping elements. The second sliding element 13 is slidably disposed within the first sliding element 6, both being composed of a rigid substance such as hard plastic. Attached to the distal end of the second sliding element 15 is the second sliding element head 9 which is rigidly integrated with second grasping element 8 including teeth 88. The first grasping element 7 is rigidly integrated with the first sliding element 6 and also includes teeth 88. On one side of the second sliding element 13, the second grasping element 8 has four teeth 88 facing towards the opposing teeth 88 of the first grasping element 7 of the first sliding element 6. The teeth 88 have at least one area where their inner surface 51 is angled at less than 90 degrees to the long axis of the distal second sliding element shaft 56, leaning into the teeth on the opposite grasping element. The second sliding element 13 and first sliding element 6 are composed of a rigid material such as hard plastic, and the second sliding element 13 is slidably disposed within the first sliding element 6 so that retraction of the second sliding element 13 using any of a variety of means described herein results in closing of the gap between the first sliding element grasper elements 7 and the second sliding element grasper elements 8, resulting in grasping of a needle 21 placed between them, as seen in FIG. 6C. The interleaved pattern of the two sets of grasping elements permits them to slide beyond each other if a needle or object were not between them. This permits use of different sizes of needles, because the graspers close down until the needle is clamped regardless of size. This also permits assembly of the device by passage of the distal end 15 of the second sliding element 13 through the second sliding element channel 11 of the first sliding element 6, simplifying manufacture and assembly by permitting a configuration of proximal second sliding element (not shown) to be larger than the second element channel 11. On the opposite side of the grasping device 1, a second needle slot 46 is created by another set of teeth 88, similar to those described above except they are positioned along an angled axis so that a needle held within them is not at an orthogonal angle to the long axis of the grasping device 1. FIG. 6C depicts the grasping of a needle 21. On the left, the second sliding element 13 is positioned distally, creating a gap between the opposing needle slots 65 on each side of the grasping device 1. On the right, the second sliding element 13 has been retracted with the needle in position between the first set of grasping elements 7 and second set of grasping elements on the side of the grasping device 1 with the straight array, holding the needle 21 in orthogonal orientation to the long axis of the grasping device 1. No needle is present on the slanted second needle slot 46, but it could be placed there in a similar way. In variation, the mechanism could be easily altered such that the second sliding element 13 pushes against the rigid first sliding element 6 instead of retracting against it.

FIG. 7A-D depict a perspective view (FIG. 7A) and a sequential longitudinal 2-dimensional section view (FIG. 7B) of the distal end of a grasping device, a cross section view with perspective detail cut-out view of a snap-on grasping element (FIG. 7C), and a perspective view of a variation (FIG. 7D). These figures highlight concepts including snap-on grasping element 96, variation of interleaved grasping element teeth 88, large grasping window 97 with plate pair 93 for objects larger than needle shafts, integrated side-to-side spanning ridge 89 on grasping element, and second flat-plate grasping plate pair 95. In FIG. 7A-B, features already described in other variations including second sliding element shaft 56 with second sliding element head 9 that travel linearly within a first sliding element 6 to actuate the closure of first 7 and second 8 grasping elements are depicted. The interleaved teeth 88 of the first 7 and second 8 grasping elements are positioned so as to be adjacent to each other as closure occurs, with each tooth 88 sliding into the recess 98 between the teeth 88 on the opposite grasping element. In this example, there are three teeth 88 on each side of the first grasping element 7, which is a replaceable and removable element that may be snapped on or off, and four teeth 88 on each side of the second grasping element 8, which is located on the second sliding element head 9. Both grasping elements include a ridge 89 which runs continuously along the vertex 90 of the angle formed by the inner surface 51 of the teeth 88 of the grasping elements. This ridge 89 is a rigid, thin strip of material which adheres to the surface of a needle small enough in diameter to be cradled in the vertex 90 of the teeth 88. Larger needles are held by the inner surfaces 51 of the teeth 88 without touching the ridge 89. The ridge 89 may be important to prevent bending of the small diameter needles associated with the alternating configuration of the opposing teeth 88, by providing a more circumferential grasping configuration. This is not as necessary for larger diameter needles which are less prone to bending. A larger grasping window 92 is depicted, and may be used to hold objects larger than needle shafts, for example a needle hub, which may be held between the grasping plate pair 93 on the second grasping element 8 and the first sliding element 6, which in variation could be located on the first grasping element 7, and also in variation could have curved configuration instead of the depicted flat configurations. On the opposite side of the device, the shapes of the teeth 94 are substantially semi-circular, providing a different contour of grasping surface which may be more suitable for some medical instruments. In this example, a ridge is not present with these arc-shaped teeth 94. An additional area for grasping small diameter objects with a flat surface that is not interleaved is depicted, showing the second plate pair 95 of the grasping elements. This may be used when a flat grasping surface is desired, when a short grasping length is desired (since it is shorter in length than the interleaved grasping mechanism), and when a small excursion of the second sliding element is desired for entry and removal of a small diameter object such as a small bore needle. FIG. 7B depicts a sequence where a small diameter needle 21, seen in cross section, placed between the second plate pair 95 as on the left. The second sliding element 13 is retracted and the needle 21 is tightly held as on the right. Depicted in FIGS. 7A-C is the snap-on removable and replaceable first grasping element 96, permitting easy changes for other configurations (not depicted) to hold objects of different shapes and sizes. The snap-on grasping element 96, which is the same as the first grasping element 7, has an opening 63 of the second sliding element aperture 23 of the grasping element 96, permitting the grasping element 96 to be slid on and off the distal second sliding element shaft 56, with tabs 64 on two surfaces serving to lock the grasping element 96 in position on the second sliding element shaft 56. The grasping element 96 is rigid, but has enough flexibility to widen very slightly to accommodate the tabs 64 as they slide over the second sliding element shaft 56 until final position is achieved, and the tabs 64 help maintain stable position. Removal is achieved in the reverse manner. FIG. 7D depicts a variation which is similar but does not use a snap-on grasping element and instead the first grasping element 7 is a rigidly fixed part of the first sliding element 6. This variation may provide the functions described for FIGS. 7A-C) except for removal or replacement of first grasping element 7. This variation offers fewer total pieces and easier manufacture and assembly.

Figure 8A:
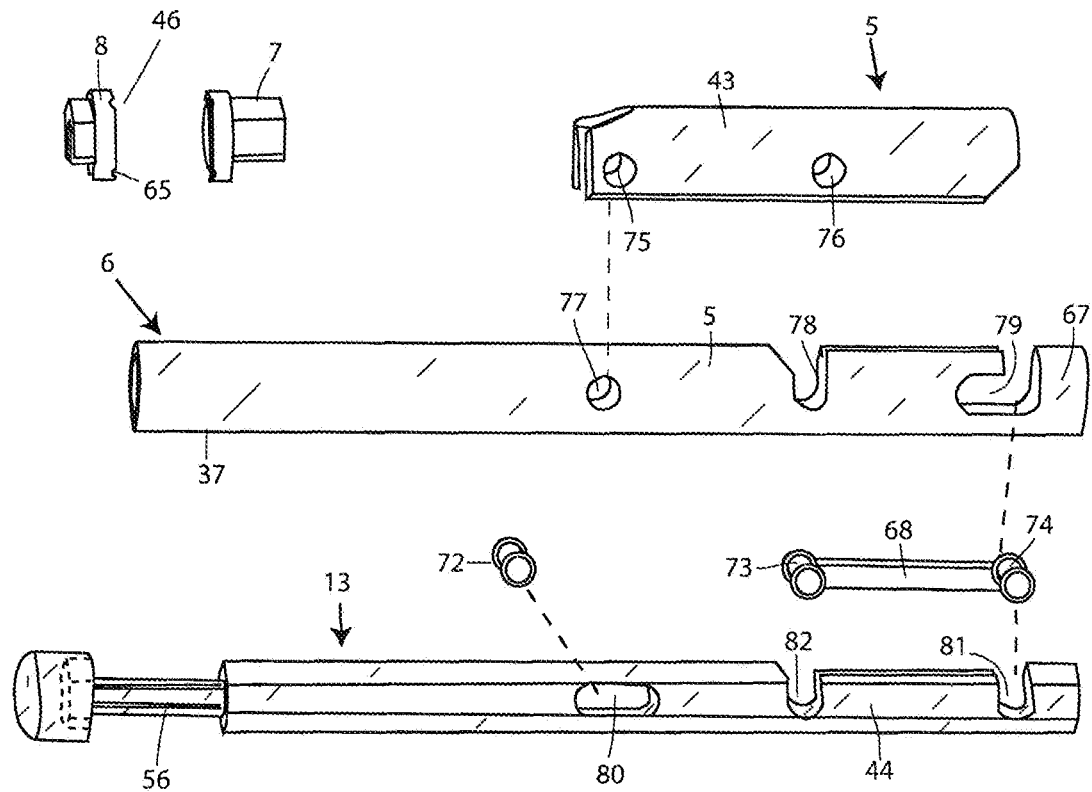
FIG. 8A-B depict an embodiment which uses a lever providing for a squeeze handle operation.
Figure 8B:
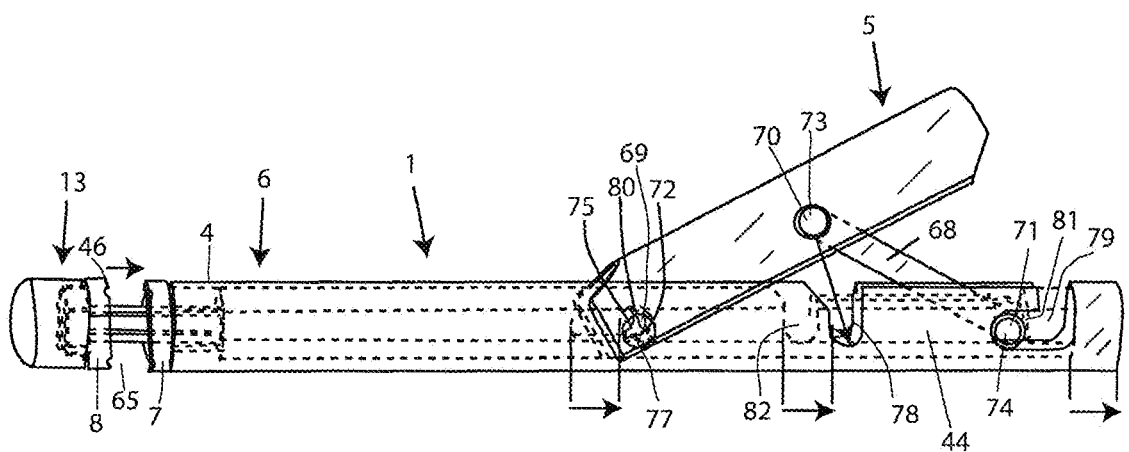

FIG. 8 A-B depict an embodiment with similar grasping mechanism as described herein, but introducing a variation of mechanism, using a lever to provide a squeeze-handle operation to provide linear motion of second sliding element 13 for grasping. FIG. 8A is an exploded view of the components, and FIG. 8B is the assembled device. In this example, the grasping elements are similar to those in FIG. 4 although many variations of grasping element described herein may be utilized. FIG. 8A-B depict first 7 and second 8 grasping elements with first needle slot 65 and second needle slot 46, second sliding element 13 with proximal shaft 44, and distal shaft 56, first sliding element 6, with distal end 37 and proximal end 67, handle 5, lever 43, rod 68 first pivot joint 69, second pivot joint 70, third pivot joint 71, first axle 72, second axle 73, third axle 74, first pivot channel 75, second pivot channel 76, third pivot-channel 77, fourth pivot channel 78, pivot rest 82, fifth pivot channel 79, sixth pivot channel 80, seventh pivot channel 81. First 7 and second 8 grasping elements are removably and slidably attached to distal end 56 of second sliding element 56 as described in FIG. 4, with first 65 and second 46 slots to hold needle or other object upon retraction of the second sliding element 13 into first sliding element 6 in a linear motion. The first pivot joint 69 includes a first axle 72 which passes through the first pivot channel 75 of the lever 43, the third pivot channel 77 of the first sliding element 6, and through the sixth pivot channel 80 of the second sliding element 13.

The second sliding element 13 is contained within the first sliding element 6, and with the lever 43 is disposed on the outer aspect of the first sliding element 6. Lever 43, first sliding element 5, and second sliding element 13 are all attached to each other by the first axle in a joint allowing rotatory motion, and also with allowance of a short distance of linear motion within the second sliding element 13 due to the elongated nature of its sixth pivot channel 80. The rod 68 is a rigid elongated structure with two axles, herein called a second axle 73 attached on one end and a third axle 74 attached on the other, both of which do not need to rotate relative to the rod 68, but are able to rotate within. At the second pivot joint 70, the second axle 73 holds the lever 43 and rod 68 together with a joint allowing rotation. The second axle 73 passes through the second pivot channel of the lever, and when the handle is depressed entirely (not shown), the second axle 73 rests in the concavity of the second sliding element 13 called the pivot rest 82. The third pivot joint 71 contains the third axle 74, which forms a rotatory joint between the rod 68, second sliding element 13, and first sliding element 6. The third axle 74 passes through the fifth pivot channel 79 of the first sliding element 6 and the seventh pivot channel 81 of the second sliding element 13. In addition to rotation, the third axle 74 has a short distance of linear slide allowed relative to second sliding element 13 due to the elongated shape of fifth pivot channel 79 of first sliding element 6. To use the grasping device 1, handle 5 is held and squeezed, causing the lever 43 to pivot at the first pivot joint 69, pushing the rod down and rearward toward the proximal end 67 of the first sliding element 6 by sliding within the elongated fifth pivot channel 79 of the first sliding element 6, and causing the second sliding element 13 to also move rearward in a linear manner as the third axle 74 pushes on the seventh pivot channel 81 of the second sliding element 13, such motion being allowed at the first pivot joint 69 due to the elongated shape of the sixth pivot channel 80. The linear motion described is suggested by the solid horizontal arrows in FIG. 8B. All elements are composed of a rigid substance such as plastic. Metallic components may be used in the handle 5 area if desired but generally not near the distal portion 4 of grasping device 1 where radio-lucency is desired.

Figure 9A:
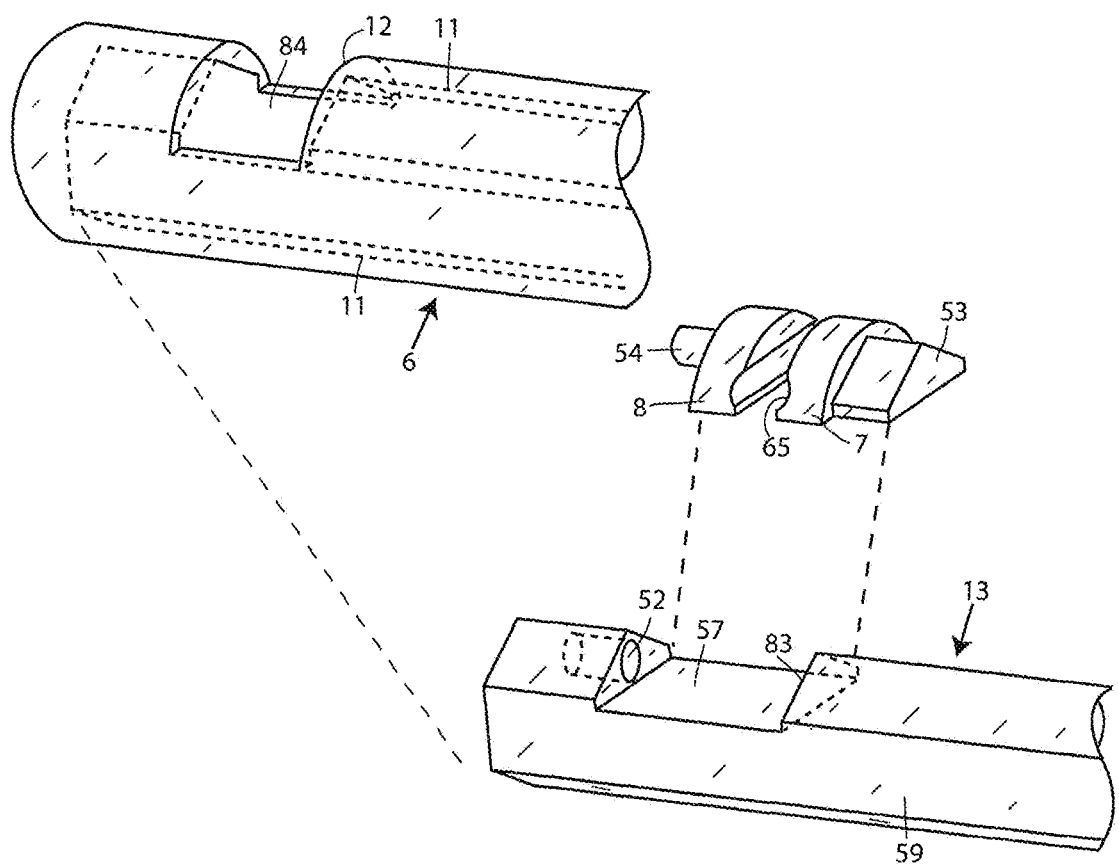
FIG. 9A-B depict an embodiment with removable grasping elements located eccentrically on the device to provide for a thicker distal second sliding element shaft without widening of the overall diameter of the device.
Figure 9B:
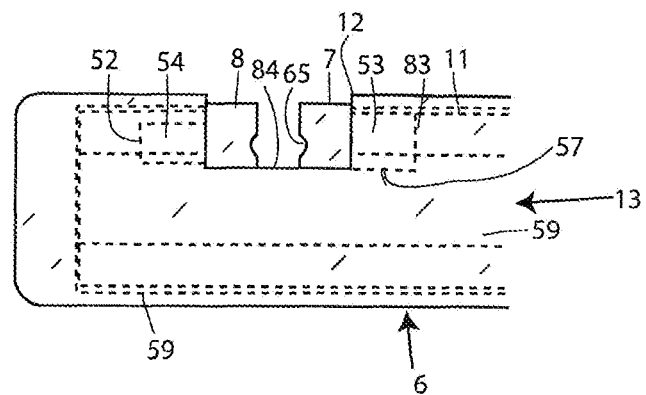
Figure 10A:
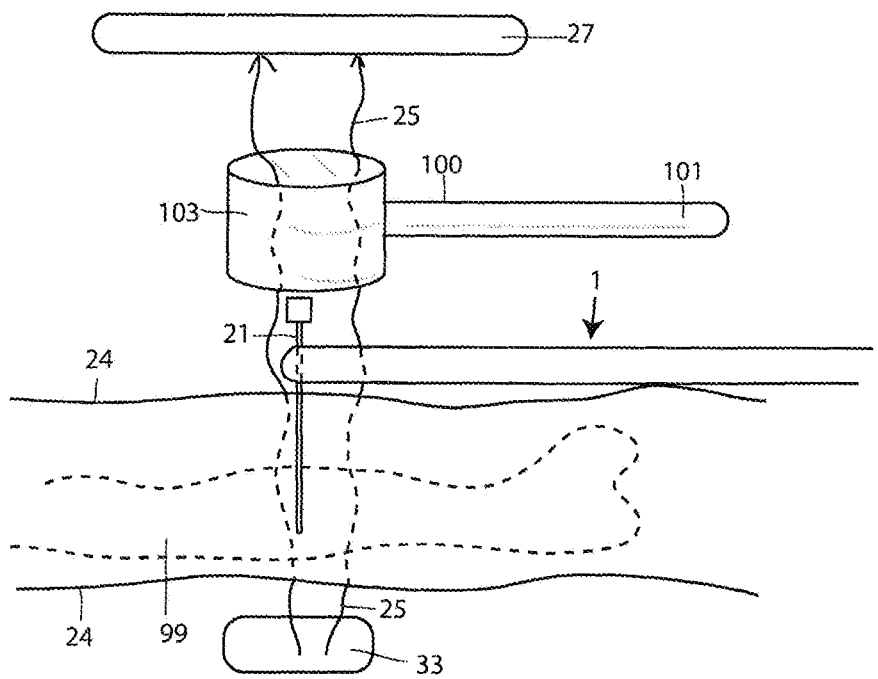
FIG. 10A-D depict embodiments and method of use of a radiolucent hammer to be used with the grasping device for pushing an instrument into hard tissues such as bone.
Figure 10B:
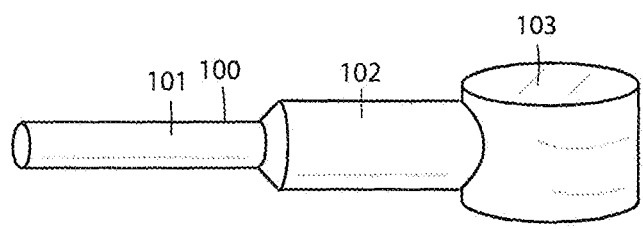
Figure 10C:
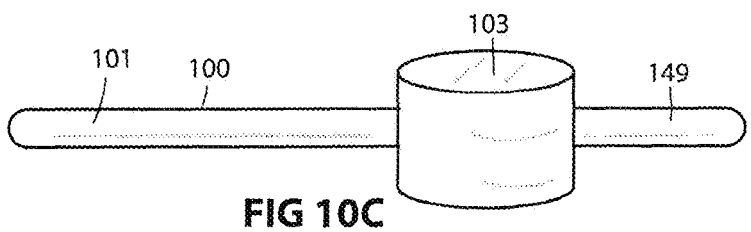
Figure 10D:
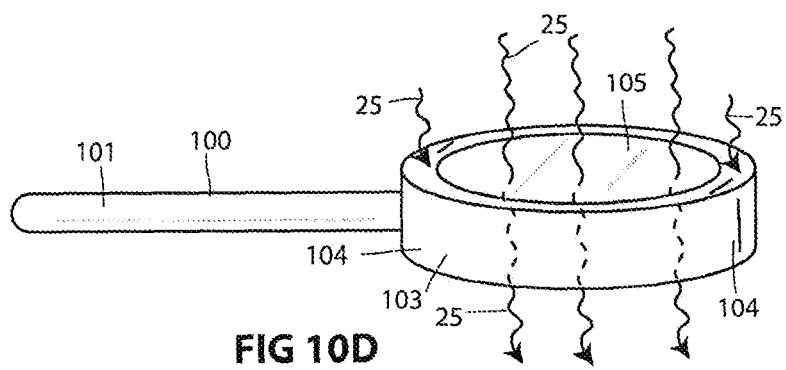

FIG. 9A-B includes an exploded perspective view (FIG. 9A) and a side view (FIG. 9B) of the distal portion another embodiment. The second sliding element 13 has a hexagonal shape in cross section, although other shapes would also be suitable. The second sliding element 13 includes a shaft notch 57 to accommodate the first 7 and second 8 grasping elements. For assembly, the second sliding element 13 is first inserted into the second sliding element channel 11 of the first sliding element 6 from its proximal end (not shown). There is a fenestration 84 in the first sliding element 6 where the second sliding element shaft notch 57 resides. The fenestration 84 is shorter in length than the second sliding element shaft notch 57. The second grasping element 8 can be placed onto the shaft notch 57 with the second engagement element 54 disposed inside the engagement cut-out 52 of the second sliding element 13. The first grasping element 7 can be placed onto the second sliding element shaft notch 57 with the first engagement element 53 abutting the wall 83 of the second sliding element 13. It becomes stabilized as its engagement element 53 is now positioned inside the second sliding element channel 11 of the first sliding element 6. The second grasping element 8 may be set upon the shaft notch 57 so that its engagement element 54 is inserted into the engagement cut-out 52 of the second sliding element 13, providing for stabilization of said grasping element. Upon linear retraction of the second sliding element 13 using any of various means described herein, the first 7 and second 8 grasping elements are brought together to hold a needle (not shown) or other object in the needle slot 65. The wall 12 of the first sliding element 6 prevents further proximal motion of the first grasping element 7.

FIG. 10 A-D include perspective views of variations of radiolucent hammers for use with grasping device. FIG. 10A depicts a simple radiolucent hammer 100 being used to drive a needle 21 into the target internal anatomic structure 99 of a patient 24. The needle 21 is being held in position by a grasping device 1 that is being held in position by the operator's hands (not depicted). X-rays 25 are emitted from the x-ray generator 33 under the patient 24, and pass through the patient table (not shown), patient 24, grasping device 1, and radiolucent hammer 100, then reach the image receptor 27 where an image is created and transmitted for viewing by the operator in real time while the hammer 100 and devices are in use. The needle 21 and internal anatomic structure 99 are relatively radio-opaque and therefore seen on imaging, importantly for achievement of the procedure, while the other radiolucent tools do not substantially interfere with their visualization, representing novel advantage over conventional tools such as conventional metallic hammers and forceps. The grasping force of the grasping device 1 may be adjusted to the desired amount so that the needle 21 is held securely in the proper trajectory, while its sliding motion within the grasping elements is still permitted when struck by the hammer 100, or pushed or rotated by the hands of the operator (not shown). The hammer-tapping method provides extremely precise preservation of desired needle position during the driving operation with "gunsight" visualization (lining up of long axis of needle with target) while keeping the operator's hands out of the x-ray field. The hammer 100 is composed of a radiolucent material such as a hard plastic. The hammer handle 101 may be composed of any rigid material including plastic or metal. The variation in FIG. 10B depicts the distal portion of the handle 102 to contain or be composed primarily of a mass of stainless steel or in variation any massive substance, to increase the mass of the hammer 100, providing more force. Another variation in FIG. 10C includes extra mass of stainless steel 102, or in variation any massive substance, attached to an extension 149 from the head 103 of the hammer on the opposite side of the handle, also to increase mass and subsequent force. Another variation in FIG. 10D has a wider head 103 with a ring 104 composed of a massive substance such as stainless steel around a radiolucent core 105 of plastic or other hard radiolucent material. The massive ring 104 blocks most of the x-rays 25 while the radiolucent core 105 permits passage and therefore visualization on imaging. All of these variations provide extra mass to the hammer 100 to provide a more forceful effect, while keeping the non-radiolucent (radio-opaque) metal out of the line of sight of the target internal anatomic structures 99 and the needle 21.

Figure 11A:
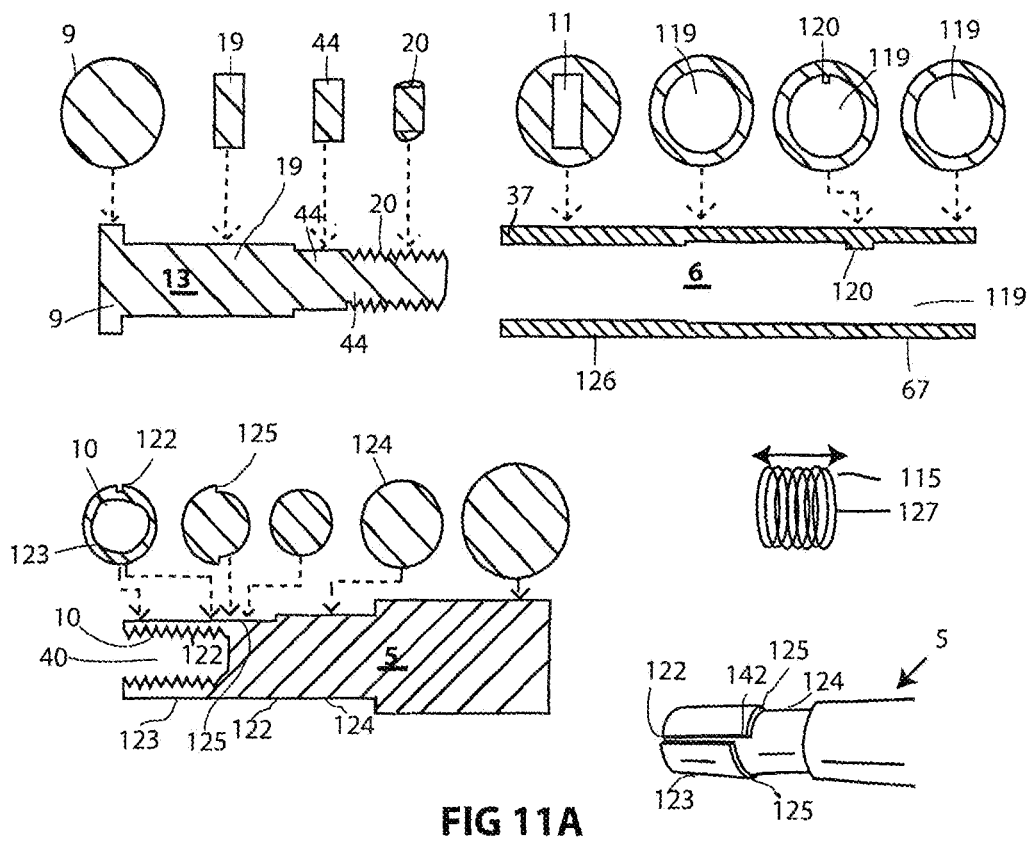
FIG. 11A-B depicts an embodiment with a spring providing for automatic grasping force, and a detent mechanism providing for prevention of inadvertent disassembly of components during use.
Figure 11B:
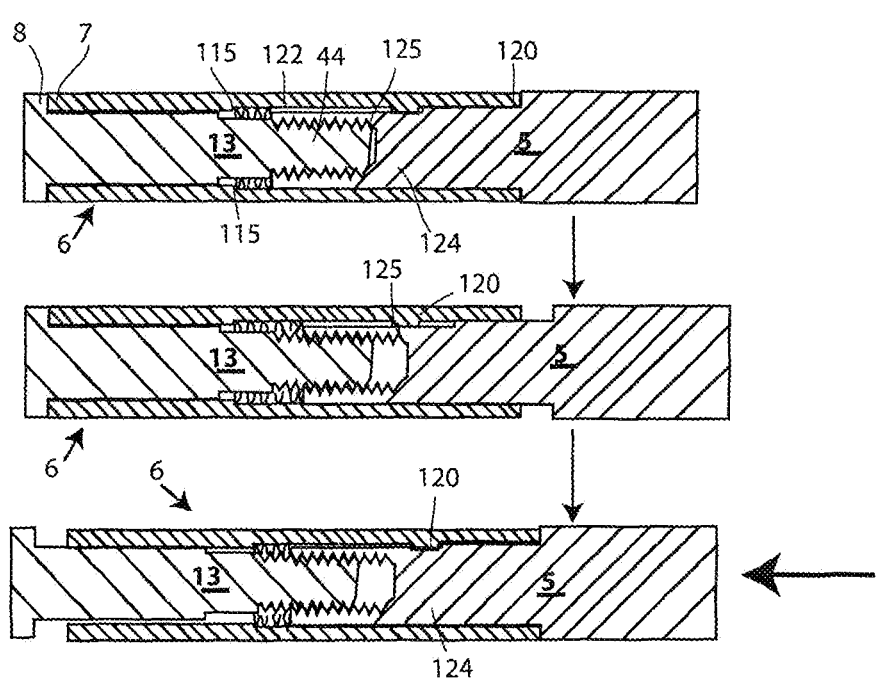

FIG. 11A-B depict a grasping device 1 which includes a spring 115 to maintain constant grasping force, and a detent 120 to prevent inadvertent disassembly during loosening of the grasping force. FIG. 11A includes exploded 2D longitudinal section views with 2D cross sectional views corresponding to locations indicated by dashed lines, as well as a side view of a spring 115 and a perspective view of the mid 124 and distal 123 portions of the handle 5. FIG. 11B is a sequential longitudinal cross sectional view of the assembled device depicting some steps of the disassembly procedure. The proximal shaft 44 and mid shaft 19 of the second sliding element 13 in this example have a rectangular shape in cross section as shown, whereas the second sliding element head 9 is round. The proximal second sliding element 44 has screw threads 20 to engage the handle 5. The proximal second sliding element 44 is smaller in diameter than the internal diameter of the coil spring 115. The first sliding element 6 is round in outer cross sectional shape, with a round inner shape on its proximal end 67, comprising a handle chamber 119, which may snugly receive the handle 5 within it. The handle chamber 119 contains a detent 120, which is a small protuberance rigidly projecting slightly into the handle chamber 119. The distal end 37 and middle 126 have a rectangular second sliding element 13. The handle 5, is round in cross section as shown, and contains a cavity 40 with screw threads 10 to engage the second sliding element screw threads 20. The handle has a channel 122 on its distal portion 123 extending longitudinally to its mid portion 124 where the outer caliber becomes narrower at the transition 125 which occurs in a gradually offset ring-like configuration. There is a transition 125 between two different calibers of the distal handle 123 and mid handle 124, and the transition is circumferential around the handle 5 but has a gradual curve out of the cross sectional plane, seen best in the perspective view. This forms a ledge 142 along the longitudinal plane which can engage the detent 120 as described herein. A conventional compression spring 115, or some other variety of spring in variation such as a compressible sleeve, is larger in outer diameter than the proximal second sliding element 44 which may pass through the spring's center 127.

To assemble the components to obtain the first (top) configuration of sequential FIG. 11B, the second sliding element 13 is passed through the first sliding element 6, the spring 115 is passed over the proximal second sliding element 44, and then the handle 5 is screwed onto the second sliding element 13. Upon insertion, the handle 5 is oriented with the channel 122 facing upwards, so it may accommodate the detent 120 of the first sliding element 6, and is pushed in far enough so that the channel 122 and transition 125 are distal to the detent 120, so that the detent 120 is located over the mid portion 124 of the handle 6. Then the handle 5 may be freely rotated clockwise, screwing the handle 5 onto the second sliding element screw threads 20, retracting the second sliding element 13, and closing the first and second grasping elements. When the handle 5 is rotated in the opposite direction (counterclockwise), the grasping elements are spread apart. The spring 115 abuts the first sliding element 6 and the handle 5 causing their separation, with resultant retraction of the second sliding element 13 since it is connected to the handle 5 by the screw threads. This maintains the detent 120 position over the mid portion 124 of the handle 5, permitting free rotation clockwise until the second sliding element 13 and handle 5 may not move any further due to abutting the ends of the first sliding element 6 and the grasping elements are fully apposed. Counterclockwise motion of the handle 5, with loosening of the grasping elements, is permitted until the second sliding element 13 extends far enough distally to bring the transition 125 of the handle 5 to the detent 120, blocking further counterclockwise rotation of the handle 5. This prevents dissociation of the handle 5 from the second sliding element 13 so that the elements to not come apart inadvertently during normal use. To defeat this detention mechanism for intentional disassembly, the handle 5 is rotated counterclockwise until the transition 125 abuts the detent 120, blocking further rotation, and resulting in the configuration of the second (middle) depiction. The first 7 and second 8 grasping elements are still closed due to the spring action.

Then the operator may push the handle forward as indicated by the arrow in the third (bottom) depiction, so that the detent 120 is again over the mid portion 124 of the handle 5, permitting further counterclockwise rotation of the handle 5, resulting in dissociation of the handle 5 and second sliding element 13 and permitting complete disassembly (not shown in sequence). Assembly of the device is achieved by performing these steps in reverse.

Figure 12A:
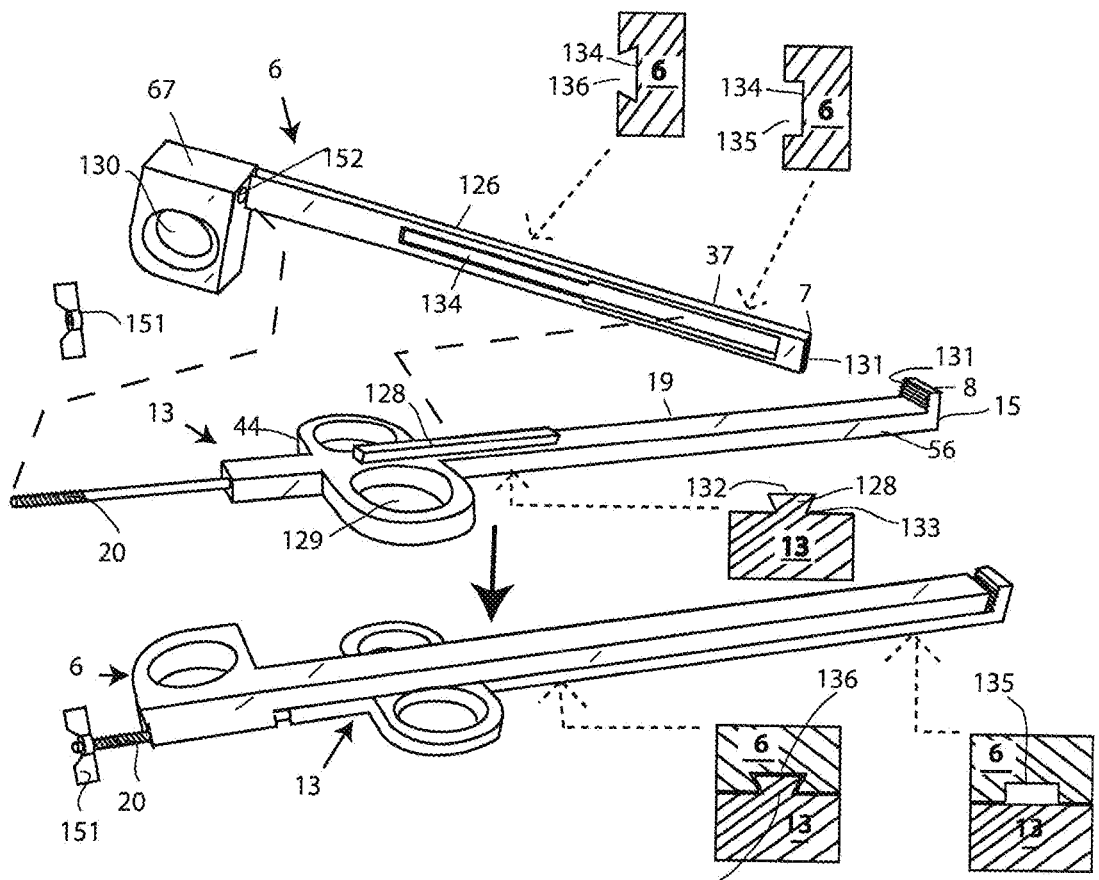
FIG. 12A-C depicts a simple embodiment with side-by-side configuration of the first and second sliding elements and use of thumb and finger rings.
Figure 12B:
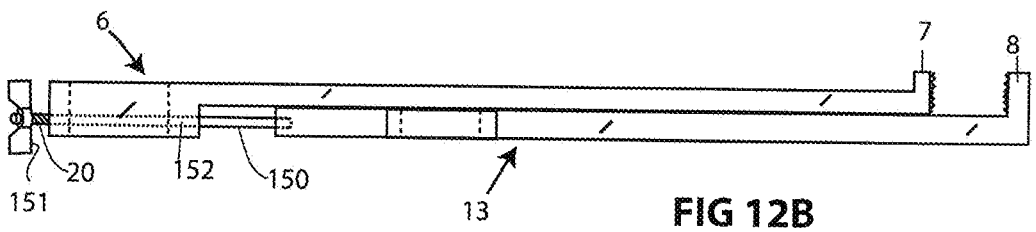
Figure 12C:
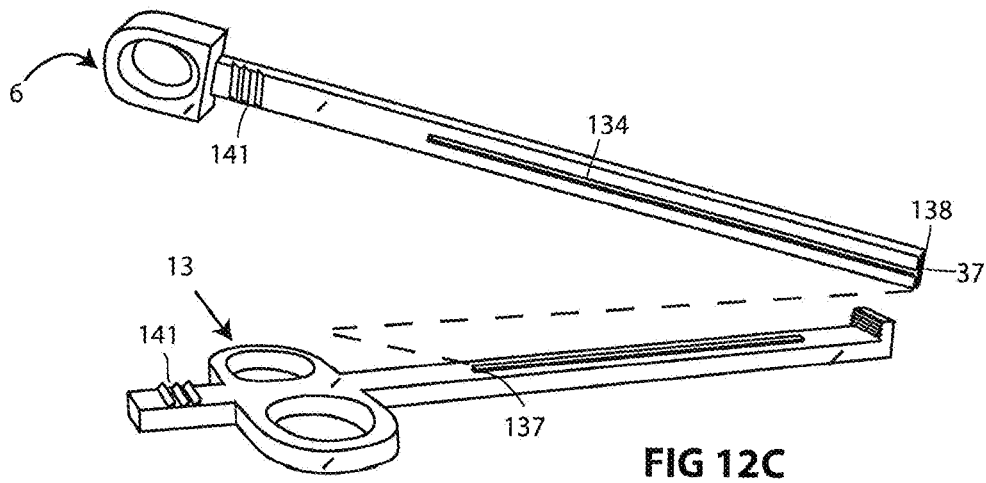

FIG. 12A-C depicts an embodiment composed of two rigid main elements including a first sliding element 6 and a second sliding element 13 which slidably attach together in an adjacent, or side-by-side configuration, allowing only sliding linear motion of said elements relative to each other, and easily controllable with one hand for motion in both directions. FIG. 12A is a sequential exploded perspective view with cross-section views at two locations as indicated by dashed lines, showing the sequence of assembly of the first sliding element 6 and second sliding element 13. FIG. 12B is a side view of the assembled device, and FIG. 12C is an exploded perspective view of another embodiment. The first sliding element 6 and second sliding element 13 may be composed of a radiolucent material such as plastic. The first sliding element 6 has a proximal portion 67, a middle portion 126 a distal portion 37. The second sliding element 13 also has a proximal portion 44, a middle portion 19, a distal portion 56, and a distal end 15. Sub-elements of the first sliding element 6 include the track 134 on the middle 126 and distal portions 37, the first grasping element 7 on the distal end 15, the thumb ring 130 on the proximal portion 67, and a hole for the second sliding element screw threads 20 to be described below. Sub-elements of the second sliding element 13 include the second grasping element 8 on the distal end 56, rail 128 in the proximal portion 44 and middle 19 portion, and the finger rings 129 on the proximal portion 44, and the second sliding element screw threads 20 on the proximal portion 44, which projects proximally, is rigidly attached and may be composed of metal or plastic or other rigid material, and does not move or rotate relative to the remainder of the second sliding element. The grasping element 7 and grasping element 8 may include surface features for better grip, or in variation, may include any other types of texture or features for providing grasp, as described in this invention or elsewhere. The features in this embodiment are serial ridges 131 which are triangular in cross section with 45 degree angle at the vertex so the opposite pairs can mesh. The thumb rings 130 and finger ring 129 are simply to improve ergonomics however in variation, the thumb and finger rings may not be actual rings but could be nearly any configuration such as a simple protrusion or even a featureless area and still provide the functions of the invention.

The rail 128 is a raised, rigid sub-element of the first sliding element 6, and is wider transversely at its top 132 than at its attachment base 133. It slides into the track 134 of the first sliding element 6. The track 134 is cavity where the inner dimensions are slightly greater than the corresponding outer dimensions of the rail 128, providing for a slidable attachment of the first sliding element 6 and second sliding element 13. In this embodiment, the track 134 is wider at its wide portion 135 which is substantially rectangular in cross section to assist assembly of the two main elements. Referring to FIG. 12 A, to assemble, the two elements are brought together as shown by the dashed lines so that the second sliding element screw threads 20 are inserted into the hole 152 through which the rod 150 is now slidably disposed because there are no screw threads in the hole 152 which is slightly wider than the second sliding element screw threads 20. Also, the rail 128 is placed into the wide portion 135 of the track 134 where the rail 128 may be inserted without slidably attaching the first 6 and second 13 sliding elements together, and then the first sliding element 6 is advanced distally so that the rail 128 becomes positioned into the narrow portion 136 of the track, where the elements become slidably attached together. A nut 151 may then be screwed onto the second sliding element screw threads 20. When the nut 151 is on the proximal end of the screws, the two main sliding elements may freely slide over each other to open and close the grasping elements as controlled by the operator's hand. Tightening the nut until it abuts the proximal portion 67 of the first sliding element will lock the device in the grasping position. Disassembly may be accomplished using reversed steps. FIG. 12B depicts the assembled invention with the first sliding element 6 withdrawn slightly, opening a gap between the first grasping element 7 and second grasping element 8, so that an object may be positioned between them. By squeezing the thumb (not depicted) and fingers (not depicted) towards each other, the first grasping element 7 and second grasping element 8 are forcefully brought together to grasp an object (not depicted). This is accomplished with a simple single-handed action.

In the embodiment depicted in FIG. 12C, the entire track 134 is a narrow portion 136 similar to the narrow portion 136 in FIGS. 12A-B, and upon referring back to FIG. 12C, the track 134 extends to the distal end 37 of the first sliding element 6. The elements are assembled by inserting the proximal end 137 of the rail 128 into the distal end 138 of the track 134 as indicated by the dotted line, and then sliding the first sliding element 6 distally. FIG. 12C also depicts another variation of ratchet locking elements 141 located on the first sliding element 6 and second sliding element 13. When the first sliding element 6 is slid proximally, the ratchet locking elements may slide over each other, but when attempting to slide in the other direction, they will lock. This lock can be defeated by bending the proximal portions of the sliding elements away from each other slightly, which may occur because these although these elements are substantially rigid, they are relatively small and capable of some bending motion.

In variation of FIG. 12A-C which is not depicted, the rail 128 may be placed on the first sliding element 6 and the track 134 may be placed on the second sliding element 13. In another variation, the second element screw threads and nut could be absent, and the device would have no locking mechanism but would be controlled by the operators hand for opening, closing, and maintain grasp.

Manufacture of this invention is relatively simple and may be achieved by plastic injection molding of the 2 main elements, which may be rapidly assembled into the functional device without tools or fasteners, at very economical cost. The second element screw threads 20 may be molded from the plastic as an integral component of the second sliding element 13, or in variation may be composed of a metal threaded rod which is rigidly attached to the second sliding element 13 by standard mechanical or adhesive means. Conventional fulcrum-based (scissors configuration) metal forceps of a large size, for example 10 inches or longer in length, might be more expensive to manufacture. The grip strength of this invention may be far greater than would be possible using a similar length and mass of plastic in a scissors-configuration forceps, where moment-arm forces are great and cause bending of the long elements. This invention therefore provides cost and function advantages over conventional large scissors-configuration plastic or metal forceps. The force applied by the hand is along the long axis of the invention, providing different mechanics for grasping which may be advantageous in some circumstances over the mechanism for conventional scissors-like forceps where the force of the hand is applied along the short axis of the device.

Figure 13A:
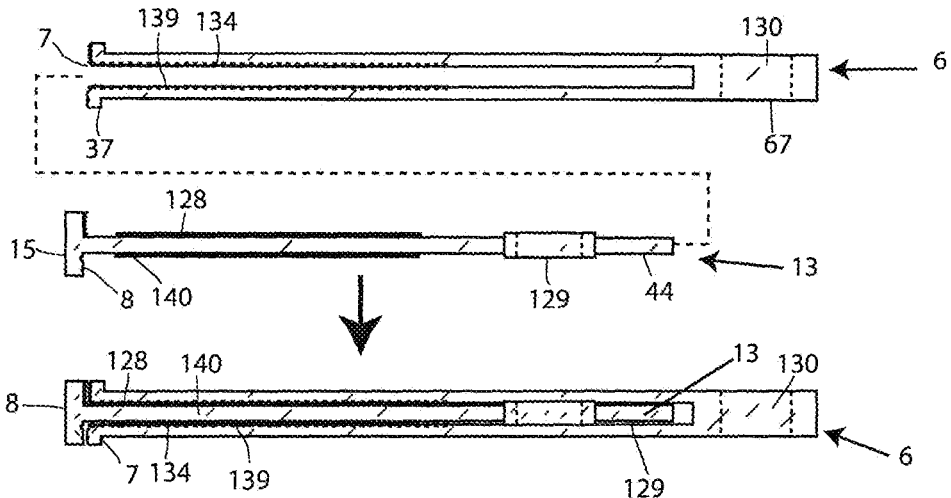
FIG. 13A-B depicts a variation with a forked configuration of the first sliding element.
Figure 13B:
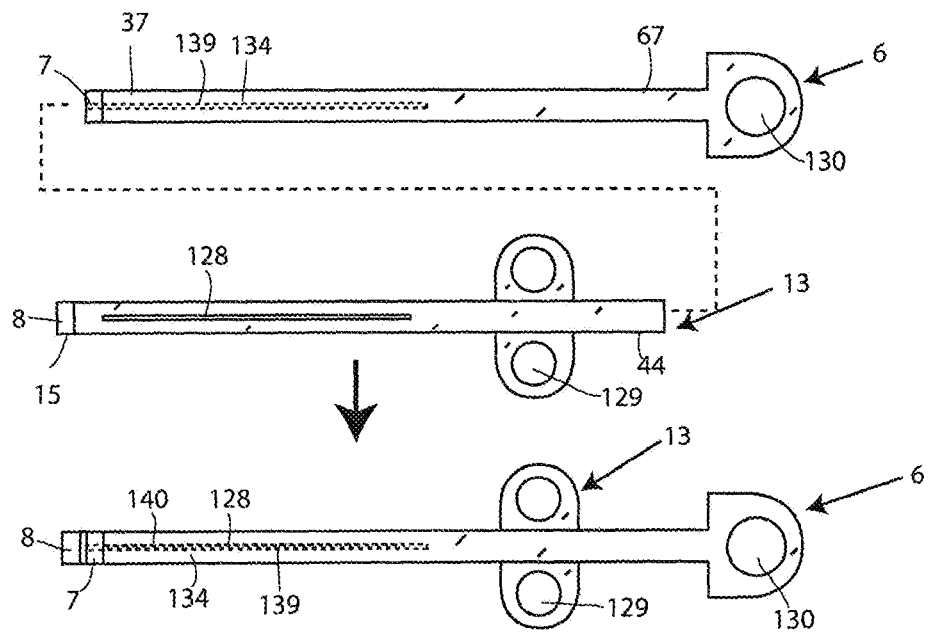

Another variation, depicted by a side sequential view in FIG. 13A and a frontal sequential view in FIG. 13B, provides for grasping with a plurality of paired grasping elements rather than the single pair depicted in, for example, FIG. 12A-C. In FIG. 13 A-B, the first sliding element 6 has a forked configuration rather than the non-forked configuration of variation in FIG. 12A-C. In FIG. 13A-B, the second sliding element 13 includes finger rings 129 on its proximal portion 4, and a first rail 128 and second rail 140 on its exterior surface, and a second grasping element 8 on its distal portion 15. The first sliding element 6 includes a thumb ring 130 in its proximal portion 67, a first track 134 on one interior surface and a second track 139 on the opposite interior surface, and a first grasping element 7 on its distal end 15, providing for different textures or architectures of the grasping elements using any type described in this invention or elsewhere. The proximal portion 44 of the second sliding element 13 may be inserted into the distal end 37 of the first sliding element 13, with the first 128 and second 140 rails sliding within the first 134 and second 139 tracks of the first sliding element, providing for assembly of device as depicted to the right of the arrows. It may now operate similarly to as described elsewhere in this invention, with operator choosing which grasping element pair to use.

Figure 14:
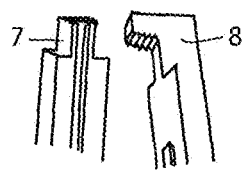
FIG. 14 depicts a variation of grasping elements which are narrow and provide for grasping of small objects such as a suture needle.

In variation, the first track 134 and second track 139 may be on the second sliding element 13 and the first rail 128 and second rail 140 may be on the first sliding element 6, and any number of grasping element pairs including one may be incorporated by modifying the distal ends of the sliding elements. An example of another grasping element configuration is depicted in the 3 dimensional view in FIG. 14, where the first grasping element 7 and second grasping element 8 have narrow footprints permitting a precise grasp of short objects such as a suture needle.

FIG. 15A-C depicts a variation resembling the embodiment in FIG. 13 with the addition of a mechanical tightening and locking mechanism to provide a secure hold on the grasped instrument, and using variations of principles described elsewhere herein including second sliding element screw threads 20. FIG. 15A is a side view of the first sliding element 6 (top), second sliding element 13 (middle), and assembled device (bottom), and FIG. 15B is an overhead view of same. FIG. 13 C is an overhead view of assembled device after action described below is taken. The first sliding element 6 has a threaded nut 151 around its proximal portion 67 which may rotate freely around the first sliding element 6 since there are no threads on the first sliding element 6. It may travel along the long axis of the first sliding element 6 freely until it abuts the widened portions on each side of it including the widened portion 153 where it is constrained. It has a configuration resembling a standard threaded nut with internal threads which engage the second sliding element threads 20 once assembled. The second sliding element threads 20 are located on the sides of the proximal portion 44 of the second sliding element, but not on its top or bottom which remain flat as best seen in the side view, and provide for a free sliding motion within the forked configuration of the first sliding element 6 once assembled, as best seen in the side view, and in a similar manner to as depicted of embodiment in FIG. 13. In FIG. 15, assembly of this embodiment is similar in most regards to that in FIG. 13 however the wide thumb ring 130 may have to be attached to the remainder of the first sliding element 6 after placement of the nut 20, using conventional mechanical or adhesive means. After assembly the device, as depicted in the bottom drawings of FIG. 15A and FIG. 15B, free sliding motion is provided for between the first 6 and second 13 sliding elements because the nut 20, which is fixed to the second sliding element 13 by their threads, slides freely on the first sliding element 6. This provides for the operator to freely open and close the grasping elements by moving the thumb and fingers closer together (to close) or farther apart (to open), similar to as depicted in embodiment in FIG. 13. In FIG. 15, When a locking grasp is desired, rotating the nut 20 will pull the second sliding element 13 proximally, and the nut will travel distally until it abuts and is restrained by the wide portion 153, resulting in the configuration depicted in FIG. 15C, where grasping elements (not depicted) are tightly opposed around the grasped instrument. This locking grasp is released by counter-rotation of the nut, to again allow free sliding motion of the first 6 and second 13 sliding elements. In variation, a spring may be added to the embodiment in FIG. 15 to provide a constant grasping force in a manner which has been described elsewhere in this invention.

FIG. 16 is a perspective view and cross sectional view of the proximal portion of a variation representing a modification of the embodiment of FIG. 12, where the first sliding element 6 is not forked and the first 6 and second 13 sliding elements are adjacent to each other. In the variation of FIG. 16, the second sliding element threads 20 span 180 degrees around the circumference of the cross-section of the first sliding element 6, and the opposing surfaces of the first 6 and second 13 sliding elements remain flat, providing for sliding motion between the first 6 and second 13 sliding elements. Similarly to as depicted in FIG. 15, in In FIG. 16, rotation of the nut 20 causes it to abut a wide portion 153 of the first sliding element 6, pulling the second sliding element 13 proximally to grasp an instrument, and lock the grasp. Similarly to as depicted in FIG. 15, in FIG. 16 when the nut 20 is counter-rotated, the lock is released and free sliding motion of the first 6 and second 13 sliding elements is allowed. Manufacture of this embodiment may require that the first sliding element 6 is composed of two pieces which are joined together using conventional mechanical or adhesive means in order to provide for placement of the nut 151 around the first sliding element 6.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the apparatus, process, machine, manufacture, composition of matter, means, methods and steps described in the specification. As one of ordinary skill in the art will readily appreciate from the disclosure, apparatus, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such apparatus, processes, machines, manufacture, compositions of matter, means, methods, or steps.

The invention claimed is:

1. An apparatus for remotely grasping a medical instrument, comprising:
   a first grasping element;
   a second grasping element disposed substantially parallel to the first grasping element; and
   a locking mechanism comprising a threaded nut and a plurality of screw threads;
   wherein the first and second grasping elements are configured to grasp the medical instrument by drawing at least one of the first and second grasping elements toward the other grasping element along a linear, non-rotational path such that the first grasping element and the second grasping element remain substantially parallel;
   wherein when the first and second grasping elements grasp the medical instrument, a circumferential force is applied to the medical instrument; and
   wherein the locking mechanism is configured for selectively locking the grasp of the first and second grasping elements on the medical instrument by rotating the threaded nut or the plurality of screw threads with respect to the other to exert a locking force on the first and second grasping elements.

2. The apparatus of claim 1, wherein the locking mechanism is configured to tighten the lock on the grasp of the first and second grasping elements on the medical instrument by further rotating the threaded nut or the plurality of screw threads with respect to the other to increase the locking force on the first and second grasping elements.

3. The apparatus of claim 1, wherein the locking mechanism is configured to unlock the grasp of the first and second grasping elements on the medical instrument by counter rotating the threaded nut or the plurality of screw threads with respect to the other to remove the locking force on the first and second grasping elements.

4. The apparatus of claim 1, wherein the first and second grasping elements are configured to release the medical instrument by drawing at least one of the first and second grasping elements away from the other grasping element.

5. The apparatus of claim 1, wherein at least a portion of the apparatus is radiolucent.

6. The apparatus of claim 1, wherein the apparatus is used to guide the medical instrument into tissue.

7. The apparatus of claim 6, wherein when the medical instrument is grasped between the first grasping element and the second grasping element, the apparatus permits sliding motion of the medical instrument when a radiolucent hammer or an operator's hand is used for driving the medical instrument into the tissue.

8. The apparatus of claim 1, wherein the first and second grasping elements comprise:
   curved depressions which align when the first and second grasping elements are drawn together.

9. The apparatus of claim 1, wherein the first and second grasping elements comprise:
   interdigitating members that form at least one slot for grasping the medical instrument when the first and second grasping elements are drawn together.

10. The apparatus of claim 9, wherein the interdigitating members comprise teeth on the second grasping element and opposing teeth on the first grasping element.

11. The apparatus of claim 10, wherein the teeth and the opposing teeth comprise angled inner surfaces.

12. The apparatus of claim 10, wherein the teeth and the opposing teeth comprise semicircular surfaces.

13. The apparatus of claim 1, wherein the first and second grasping elements comprise:
   angled slots for grasping the medical instrument at an oblique angle.

14. The apparatus of claim 1, further comprising:
a first sliding element coupled to the first grasping element; and
a second sliding element coupled to the second grasping element;
wherein at least one of the first and second sliding elements slides with respect to the other to cause the first and second grasping elements to grasp the medical instrument.

15. The apparatus of claim 14, wherein the screw threads of the locking mechanism are coupled to either the first sliding element or the second sliding element.

16. The apparatus of claim 15, wherein the screw threads are coupled only to two opposing sides of the relevant sliding element, and wherein the other sliding element has no screw threads.

17. The apparatus of claim 16, wherein when the threaded nut of the locking mechanism is rotated with respect to the screw threads, the sliding element to which the screw threads are coupled is retracted with respect to the other sliding element until the threaded nut engages a widened portion on the other sliding element to lock the grasp of the first and second grasping elements on the medical instrument.

18. The apparatus of claim 14, wherein the threaded nut of the locking mechanism is coupled to either the first sliding element or the second sliding element.

19. The apparatus of claim 14, wherein the apparatus is configured for one-hand operation to cause the first and second grasping elements to grasp the medical instrument.

20. The apparatus of claim 14, wherein the first sliding element or the second sliding element is at least partially housed within the other.

21. The apparatus of claim 14, further comprising a spring mechanism coupled to one of the first and second sliding elements for maintaining a constant grasping force.

22. The apparatus of claim 14, further comprising a detent coupled to one of the first and second sliding elements, the detent configured to interact with the other of the first and second sliding elements to prevent inadvertent disassembly of the sliding elements.

23. The apparatus of claim 14, wherein at least one of the first and second sliding elements has a forked configuration.

24. The apparatus of claim 22, further comprising:
a track on one of the first and second sliding elements;
a rail on the other of the first and second sliding elements;
wherein the rail fits within the track to maintain a linear sliding arrangement between the first sliding element and the second sliding element.

* * * * *